(12) United States Patent
Zhang et al.

(10) Patent No.: US 11,560,545 B2
(45) Date of Patent: Jan. 24, 2023

(54) POLYMERIC CARRIERS AND METHODS

(71) Applicants: The Brigham and Women's Hospital, Inc., Boston, MA (US); Lonza Walkersville Inc., Walkersville, MD (US)

(72) Inventors: Yi Zhang, Cambridge, MA (US); Natalie Artzi, Brookline, MA (US); Kui Wang, Quincy, MA (US); Eytan Abraham, Potomac, MD (US); Yonatan Levinson, Walkersville, MD (US)

(73) Assignees: Lonza Walkersville Inc., Walkersville, MD (US); The Brigham and Women's Hospital, Inc., Boston, MA (US); Massachusetts Institute of Technology, Cambridge, MA (US)

( * ) Notice: Subject to any disclaimer, the term of this patent is extended or adjusted under 35 U.S.C. 154(b) by 432 days.

(21) Appl. No.: 16/610,325

(22) PCT Filed: May 1, 2018

(86) PCT No.: PCT/US2018/030479
§ 371 (c)(1),
(2) Date: Nov. 1, 2019

(87) PCT Pub. No.: WO2018/204381
PCT Pub. Date: Nov. 8, 2018

(65) Prior Publication Data
US 2020/0080051 A1   Mar. 12, 2020

Related U.S. Application Data

(60) Provisional application No. 62/500,232, filed on May 2, 2017.

(51) Int. Cl.
| | |
|---|---|
| *C12N 5/00* | (2006.01) |
| *C08L 5/02* | (2006.01) |
| *C08L 5/04* | (2006.01) |
| *C08L 5/08* | (2006.01) |
| *C08L 5/12* | (2006.01) |
| *C12N 5/0775* | (2010.01) |
| *C08K 5/372* | (2006.01) |
| *C08K 5/378* | (2006.01) |

(52) U.S. Cl.
CPC .............. *C12N 5/0075* (2013.01); *C08L 5/02* (2013.01); *C08L 5/04* (2013.01); *C08L 5/08* (2013.01); *C08L 5/12* (2013.01); *C12N 5/0663* (2013.01); *C08K 5/378* (2013.01); *C08K 5/3725* (2013.01); *C08L 2312/00* (2013.01); *C12N 2531/00* (2013.01); *C12N 2533/18* (2013.01); *C12N 2533/40* (2013.01); *C12N 2533/72* (2013.01); *C12N 2533/74* (2013.01); *C12N 2533/76* (2013.01); *C12N 2533/80* (2013.01); *C12N 2537/10* (2013.01)

(58) Field of Classification Search
CPC ...... C08L 5/04; C08L 5/08; C08L 5/02; C08L 5/12; C08L 2312/00; C12N 5/0662; C12N 5/0075; C12N 5/0663; C12N 2533/18; C12N 2533/74; C12N 2533/80; C12N 2531/00; C08K 5/378
See application file for complete search history.

(56) References Cited

U.S. PATENT DOCUMENTS

2014/0080214 A1   3/2014  Nugraha et al.
2016/0304832 A1*  10/2016  Hariri .................. C12N 5/0668

FOREIGN PATENT DOCUMENTS

JP            3014318 B2 *   2/2000

OTHER PUBLICATIONS

Akin et al. Preparation and Characterization of Crosslinked Gelatin Microspheres. Journal of Applied Polymer Science (1995), 58, 95-100; (Year: 1995).*
Rasmussen et al. Glutaraldehyde. The Influence of pH, Temperature, and Buffering on the Polymerization Rate. Histochemistry (1974), 38, 19-26 (Year: 1974).*
Hwang et al. Stop-Flow Lithography for the Production of Shape-Evolving Degradable Microgel Particles. J. Am. Chem. Soc. (2009), 131(12), 4499-4504. (Year: 2009).*
Eibes et al. Maximizing the ex vivo expansion of human mesenchymal stem cells using a microcarrier-based stirred culture system. Journal of Biotechnology (2010), 146, 194-197 (Year: 2010).*
T.R. Keenan. Gelatin. Kirk-Othmer Encyclopedia of Chemical Technology (2000), 20 page reprint. (Year: 2000).*
Solorio et al. Engineered cartilage via self-assembled hMSC sheets with incorporated biodegradable gelatin microspheres releasing transforming growth factor-β31. Journal of Controlled Release (2012), 158, 224-232. (Year: 2012).*

(Continued)

*Primary Examiner* — Sean C. Barron
(74) *Attorney, Agent, or Firm* — Eversheds Sutherland (US) LLP

(57) ABSTRACT

Provided are methods of controlling disassociation of cells from a carrier, compositions, and methods of collecting cells. The methods of controlling disassociation of cells from a carrier may include contacting a polymeric carrier with one or more digesting agents to disassociate at least a portion of a plurality of cells from the polymeric carrier. The polymeric carrier may be crosslinked with a crosslinker including at least one of a redox sensitive moiety, a UV light sensitive moiety, a pH sensitive moiety, and a temperature sensitive moiety.

15 Claims, 13 Drawing Sheets

(56) References Cited

OTHER PUBLICATIONS

Sakamoto et al. Reversible Crosslinking in Cellulose. 11. Monoand Bifunctional Reactions of Bis-p-isocyanatoethyl Disulfide with Cotton. Journal of Polymer Science (1970), 14, 865-878. (Year: 1970).*
PCT International Search Report and Written Opinion for PCT Application No. PCT/US2018/030479 dated Aug. 7, 2018 (12 pages).
Li et al., "Alginate/PEG Based Microcarriers with Cleavable Crosslinkage for Expansion and Non-lnvasive Harvest of Human Umbilical Cord Blood Mesenchymal Stem Cells," Materials Science and Engineering, 2016, C64:43-53.
Pettersson et al., "Cell Expansion of Human Articular Chondrocytes on Macroporous Gelatine Scaffolds—Impact of Microcarrier Selection on Cell Proliferation," Biomed. Mater., 2011, vol. 6 (13 pages).
Shu et al., "Disulfide-Crosslinked Hyaluronan-Gelatin Hydrogel Films: A Covalent Mimic of the Extracellular Matrix for in vitro Cell Growth," Biomaterials, 2003, 24:3825-3834.
Tamura et al., "Click-Crosslinkable and Photodegradable Gelatin Hydrogels for Cytocompatible Optical Cell Manipulation in Natural Environment," Scientific Reports, 2015, 5:15060 (12 pages).
Tamura et al., "Optical Cell Separation from Three-Dimensional Environment in Photodegradable Hydrogels for Pure Culture Techniques," Scientific Reports, 2014, 4:4793 (6 pages).
Zhang et al., "Engineered Extracellular Matrices with Cleavable Crosslinkers for Cell Expansion and Easy Cell Recovery," Biomaterials, 2008, 29:4521-4531.

\* cited by examiner

POLYMERIC CARRIERS AND METHODS

CROSS-REFERENCE TO RELATED APPLICATIONS

This application claims priority to U.S. patent application Ser. No. 62/500,232, filed May 2, 2017, which is incorporated herein by reference.

BACKGROUND

Crosslinked porous gelatin microcarriers are widely used as a cell substrate for cell therapy applications. For example, Cultispher-G is a porcine gelatin-based porous microsphere, which is widely used as a microcarrier for adherent cell suspension culture and expansion. The porous structure of Cultispher-G beads may increase the surface area available for cell attachment and proliferation. Moreover, gelatin, which is derived from collagen, is one of the main components of the extracellular matrix, and, therefore, can provide binding motifs for cell attachment.

Gelatin also is digestible via proteolytic enzymes, which enables facile cell dissociation from the porous gelatin microcarriers, as well as a simplified downstream process while maintaining cell viability.

However, the production of extracellular matrix by the highly dense cells usually slows the complete digestion of the porous gelatin microcarriers, thereby undesirably delaying the disassociation of the cells. This can result in low cell recovery, low cell viability, suboptimal biological properties, or a combination thereof, which can hinder the use of porous gelatin microcarriers in clinical applications.

There remains a need to improve compositions and methods for better control of digestion time, cell recovery, and/or cell viability.

BRIEF SUMMARY

Improved compositions, methods of controlling disassociation of cells from a carrier, and methods of collecting cells have been developed which address one or more of the above-described needs.

In one aspect, methods of controlling disassociation of cells from a carrier are provided. In some embodiments, the methods include providing a polymeric carrier and a plurality of cells adhered to the polymeric carrier; and contacting the polymeric carrier with one or more digesting agents to disassociate at least a portion of the plurality of cells from the polymeric carrier; wherein the polymeric carrier is crosslinked with a crosslinker including at least one of a redox sensitive moiety, a UV light sensitive moiety, a pH sensitive moiety, and a temperature sensitive moiety. In some embodiments, the crosslinker includes the redox sensitive moiety, and the redox sensitive moiety includes a disulfide bond. In some embodiments, the redox sensitive moiety includes a disulfide bond, and the one or more digesting agents includes a reducing agent. In some embodiments, the crosslinker includes the UV light sensitive moiety, and the UV light sensitive moiety is a photoreversibly dimerizable moiety or a photocleavable moiety. The photoreversibly dimerizable moiety may include a coumarin derivative. The photocleavable moiety may include an o-nitrobenzene based photolabile group.

In some embodiments, the methods of controlling disassociation of cells from a carrier include providing a photocrosslinked gelatin carrier and a plurality of cells adhered to the photocrosslinked gelatin carrier; and contacting the photocrosslinked gelatin carrier with one or more digesting agents to disassociate at least a portion of the plurality of cells from the gelatin carrier; wherein the photocrosslinked gelatin carrier includes UV light-induced free radical crosslinking.

In another aspect, compositions are provided herein. In some embodiments, the compositions include a crosslinked polymeric bead including a crosslinker having at least one disulfide bond; and a plurality of cells adhered to the crosslinked polymeric bead. In some embodiments, the compositions include a plurality of Cultispher-G beads crosslinked with hexamethylene diisocyanate, wherein the ratio of hexamethylene diisocyanate (mmol) to the plurality of Cultsipher-G beads (g) is about 0.1 mmol:10 g to about 1.9 mmol:10 g. In some embodiments, the ratio of hexamethylene diisocyanate (mmol) to the plurality of Cultsipher-G beads (g) is about 0.5 mmol:10 g to about 1.0 mmol:10 g. In some embodiments, the compositions include a polymeric carrier crosslinked with a crosslinker including at least one of a redox sensitive moiety, a UV light sensitive moiety, a pH sensitive moiety, and a temperature sensitive moiety. The compositions provided herein may include a plurality of cells adhered to the polymeric carrier.

In another aspect, methods of collecting cells are provided. In some embodiments, the methods include disposing a polymeric carrier provided herein in a medium including a plurality of cells under conditions sufficient to facilitate adherence of at least a portion of the plurality of cells to the polymeric carrier.

The carriers of the methods and compositions provided herein generally can be of any size and/or shape. In some embodiments, the carriers are microcarriers. The carriers also may have larger structures, including any 2D or 3D construct.

Other objects, features, and advantages of the invention will be apparent from the following detailed description, drawings, and claims. Unless otherwise defined, all technical and scientific terms and abbreviations used herein have the same meaning as commonly understood by one of ordinary skill in the art to which this invention pertains. Although methods and compositions similar or equivalent to those described herein can be used in the practice of the present invention, suitable methods and compositions are described without intending that any such methods and compositions limit the invention herein.

DETAILED DESCRIPTION

Figure 1A:
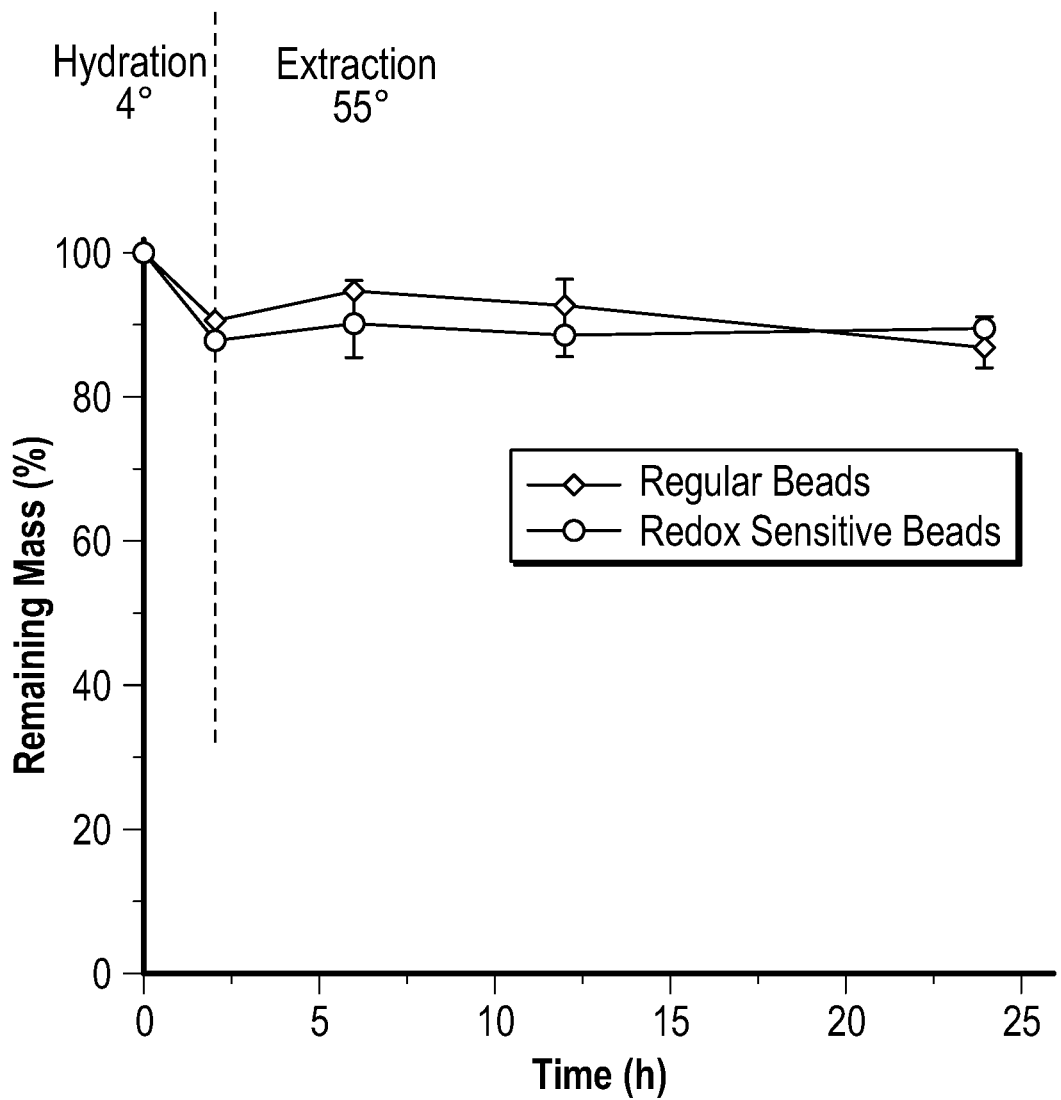
FIG. 1A depicts the results of an extraction study conducted on two types of Cultispher-G beads, including an embodiment of a redox sensitive Cultispher-G bead.

Improved compositions and methods of addressing one or more of the disadvantages associated with known carriers have been developed. In one aspect, polymeric carriers are provided that are crosslinked with crosslinkers that are redox sensitive, UV light sensitive, pH sensitive, temperature sensitive, or a combination thereof. Also provided herein are polymeric carriers having variable degrees of crosslinking and/or UV light-induced free radical crosslinking. The polymeric carriers provided herein may digest faster than known carriers, and/or be digested by mechanisms other than proteolytically cleaving the carrier due, at least in part, to the fact that the sensitivities of the crosslinkers may be exploited.

Methods of Controlling Disassociation of Cells from a Carrier

Methods of controlling disassociation of cells from a carrier are provided herein. In some embodiments, the methods include providing a polymeric carrier and a plurality of cells adhered to the polymeric carrier; and contacting the polymeric carrier with one or more digesting agents to disassociate at least a portion of the plurality of cells from the polymeric carrier. The polymeric carrier may be crosslinked with a crosslinker that includes a redox sensitive moiety, a UV light sensitive moiety, a pH sensitive moiety, a temperature sensitive moiety, or a combination thereof. A "redox sensitive moiety," "UV light sensitive moiety," "pH sensitive moiety," or "temperature sensitive moiety" is a moiety that permits the digestion of the carrier and/or allows the digestion time of the carrier to be altered, e.g., reduced, by [1] contacting the moiety with a reducing or oxidizing agent, [2] exposing the moiety to one or more wavelengths of light, including UV light, [3] adjusting the pH of the moiety's environment, or [4] exposing the moiety to a particular temperature or range of temperatures, respectively. Cells are "adhered" to a carrier when the cells are at least partially entrapped in and/or attached to the carrier. An example of cells "attached" to a carrier includes cells that proliferate on a surface of a carrier.

When the crosslinker includes a UV light sensitive moiety, the UV light sensitive moiety may be a photoreversibly dimerizable moiety or photocleavable moiety. Therefore, the step of providing the polymeric carrier and the plurality of cells may include the following steps, which may be performed in any order and/or at least partially simultaneously: contacting the polymeric carrier with a crosslinker including a photoreversibly dimerizable moiety to conjugate the crosslinker to the polymeric carrier; and contacting the photoreversibly dimerizable moiety with UV light having a wavelength sufficient to dimerize the photoreversibly dimerizable moiety. The methods may include contacting a photoreversibly dimerizable moiety or a photocleavable moiety with UV light having a wavelength sufficient to cleave the dimerized photoreversibly dimerizable moiety or the photocleavable moiety, respectively, prior to, during, and/or after the step of contacting the polymeric carrier with the one or more digesting agents.

In some embodiments, the methods of digesting materials include providing a photocrosslinked gelatin carrier and a plurality of cells adhered to the photocrosslinked gelatin carrier; and contacting the photocrosslinked gelatin carrier with one or more digesting agents to disassociate at least a portion of the plurality of cells from the gelatin carrier; wherein the photocrosslinked gelatin carrier includes UV light-induced free radical crosslinking. The step of providing the photocrosslinked gelatin carrier and the plurality of cells may include contacting the gelatin carrier with UV light at a wavelength sufficient to induce the free radical crosslinking.

Compositions

Compositions also are provided herein. The compositions may include a polymeric carrier including a crosslinker. The crosslinker may include at least one of a redox sensitive moiety, a UV light sensitive moiety, a pH sensitive moiety, and a temperature sensitive moiety. A plurality of cells may be adhered to the polymeric carrier. In some embodiments, the crosslinker includes a redox sensitive moiety, such as a disulfide bond.

Figure 10:
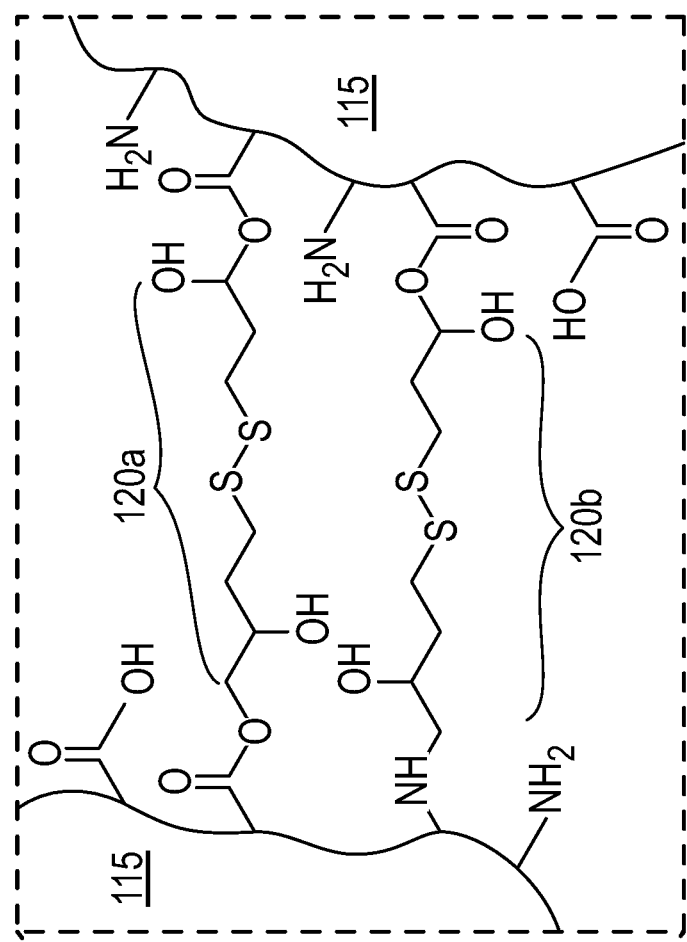
FIG. 10 depicts an embodiment of a crosslinked polymeric bead that includes crosslinkers having at least one disulfide bond.
Figure 10:
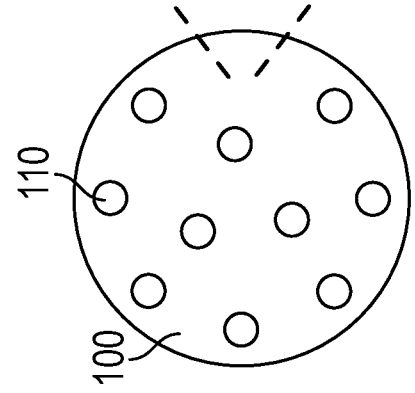

In some embodiments, the compositions include a crosslinked polymeric bead including a crosslinker having at least one disulfide bond; and a plurality of cells adhered to the crosslinked polymeric bead. For example, the composition of FIG. 10 includes a crosslinked polymeric bead 100 to which a plurality of cells 110 are adhered. The crosslinked polymer bead 100 includes a gelatin 115 that is crosslinked (120a, 120b) with crosslinkers having at least one disulfide bond.

In some embodiments, the compositions include a plurality of Cultispher-G beads crosslinked with hexamethylene diisocyanate, wherein the ratio of hexamethylene diisocyanate (mmol) to the plurality of Cultsipher-G beads (g) is about 0.1 mmol:10 g to about 1.9 mmol:10 g. In some embodiments, the ratio of hexamethylene diisocyanate (mmol) to the plurality of Cultsipher-G beads (g) is about 0.5 mmol:10 g to about 1.0 mmol:10 g.

Methods of Collecting Cells

Methods of collecting cells also are provided herein. In some embodiments, the methods of collecting cells include disposing any of the polymeric carriers provided herein in a medium including a plurality of cells under conditions sufficient to facilitate adherence of at least a portion of the plurality of cells to the polymeric carriers. For example, the polymeric carrier disclosed in the medium may include [1] a polymeric carrier including a crosslinker selected from at least one of a redox sensitive moiety, a UV light sensitive moiety, a pH sensitive moiety, and a temperature sensitive moiety, [2] a crosslinked polymeric bead including a crosslinker having at least one disulfide bond, or [3] a plurality of Cultispher-G beads crosslinked with hexamethylene diisocyanate, wherein the ratio of hexamethylene diisocyanate (mmol) to the plurality of Cultsipher-G beads (g) is about 0.1 mmol:10 g to about 1.9 mmol:10 g.

Polymeric Carriers

The polymeric carriers may include any biocompatible polymeric material, such as one or more biocompatible polymers, one or more biocompatible co-polymers, or any combination thereof. In some embodiments, the polymeric carriers include a crosslinked biocompatible polymeric material. In some embodiments, the polymeric carrier includes a biocompatible polymeric material that is not crosslinked.

Non-limiting examples of biocompatible polymeric materials include gelatin, dextran, hyaluronic acid, agarose, chitosan, alginate, polyvinyl alcohol, polyamino acids, calcium alginate, polyacrylate, polyethylene glycol, polyethylene imine, polyanhydride, or a combination thereof.

In some embodiments, the polymeric carrier is a gelatin carrier. The gelatin may be crosslinked. In some embodiments, the gelatin carrier is a Cultispher-G carrier. The Cultispher-G carrier may be crosslinked or non-crosslinked. The Cultispher-G carrier may be in the form of a bead.

The carriers of the methods and compositions provided herein generally can be of any size and/or shape that may be suitable for a particular application.

The polymeric carriers may be of any shape that permits the adherence of cells to the polymeric carriers. In some embodiments, the polymeric carrier is in the shape of a bead, a fiber, a disk, flake, film, or a combination thereof. A plurality of the beads, fibers, disks, flakes, films, or a combination thereof may be used as the polymeric carrier. When the polymeric carrier is or includes a portion that is in the shape of a fiber, the fiber may be woven, non-woven, or a combination thereof.

In some embodiments, the polymeric carriers are microcarriers. A "microcarrier" may include any carrier having an average largest dimension of about 100 μm to about 1,000 μm. In some embodiments, the microcarriers include carriers having an average largest dimension of about 130 μm to about 380 μm. The "average largest dimension" is the average diameter of the polymeric carriers when the polymeric carriers are spherical, i.e., a bead. The carriers also may include larger, macrocarriers, which may be in the form of any 2D or 3D construct. A "macrocarrier" may include any carrier having an average largest dimension greater than 1 mm. For example, a macrocarrier may have an average largest dimension of about 1.01 mm to about 50 mm. Other dimensions are envisioned, including larger dimensions that are suitable for particular applications.

The carriers also may be porous, non-porous, or a combination thereof. For example, a composition may include a plurality of porous carriers, a plurality of non-porous carriers, or a combination thereof. As a further example, a composition might include a plurality of carriers of a particular shape, such as a bead, and the structure of each bead may include a porous portion and a non-porous portion. In some embodiments, the carrier includes a porous bead.

Crosslinkers

The crosslinkers used to crosslink the polymeric carriers provided herein may include two or more moieties capable of forming a covalent bond with one or more of the polymeric materials of the polymeric carriers.

The polymeric carrier may be crosslinked with a crosslinker including at least one of a redox sensitive moiety, a UV light sensitive moiety, a pH sensitive moiety, and a temperature sensitive moiety. In some embodiments, the crosslinker includes a redox sensitive moiety. In some embodiments, the crosslinker includes a UV light sensitive moiety. In some embodiments, the crosslinker includes a pH sensitive moiety. In some embodiments, the crosslinker includes a temperature sensitive moiety. The crosslinker may include any combination of a redox sensitive moiety, a UV light sensitive moiety, a pH sensitive moiety, and a temperature sensitive moiety. For example, the crosslinker may include a redox sensitive moiety and a UV light sensitive moiety.

When the crosslinker includes a redox sensitive moiety, the redox sensitive moiety may include a disulfide bond. In some embodiments, the crosslinker includes a compound having the following structure:

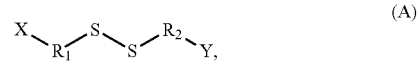

(A)

wherein $R_1$ and $R_2$ are independently selected from a divalent $C_1$-$C_{20}$ hydrocarbyl, and X and Y are independently selected from an isocyanate, an epoxide, or an N-hydroxysuccinimide ester moiety. The isocyanate, epoxide, and N-hydroxysuccinimide ester moieties may react with and form covalent bonds with embodiments of the polymeric carriers.

In some embodiments, the crosslinker includes a compound according to formula (A), wherein X and Y are an isocyanate, and the crosslinker has the following structure:

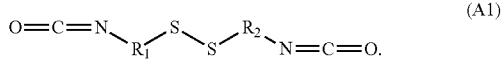

(A1)

In some embodiments, the crosslinker includes a compound according to formula (A1), wherein $R_1$ and $R_2$ are unsubstituted divalent $C_1$-$C_5$ hydrocarbyls, and the crosslinker has the following structure:

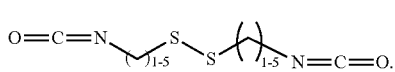
(A2)

In some embodiments, the crosslinker includes a compound of formula (A1), wherein $R_1$ and $R_2$ are unsubstituted divalent $C_2$ hydrocarbyls, and the crosslinker includes 1,2-bis-(2-isocyanatoethyl)disulfide (DIDS):

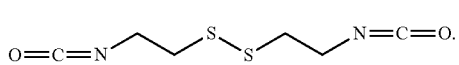
(A3)

Although the crosslinkers herein may be shown in their independent, unreacted form, it is understood by persons of ordinary skill in the art that the chemical structures of the crosslinkers typically are altered when one or both of their ends groups react with a polymeric carrier.

In some embodiments, the crosslinker includes a compound of formula (A), wherein X and Y are epoxides, and the crosslinker has the following structure:

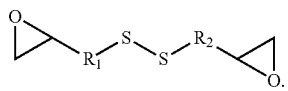
(A4)

In some embodiments, the crosslinker includes a compound of formula (A4), wherein $R_1$ and $R_2$ are unsubstituted divalent $C_1$-$C_5$ hydrocarbyls, and the crosslinker has the following structure:

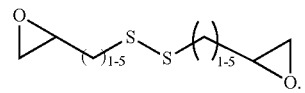
(A5)

In some embodiments, the crosslinker includes a compound of formula (A4), wherein $R_1$ and $R_2$ are unsubstituted divalent $C_2$ hydrocarbyls, and the crosslinker includes 1,2-bis(2-(oxiran-2-yl)ethyl)disulfane:

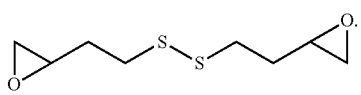
(A6)

In some embodiments, the crosslinker includes a compound of formula (A), wherein X and Y are N-hydroxysuccinimide ester moieties, and the crosslinker has the following structure:

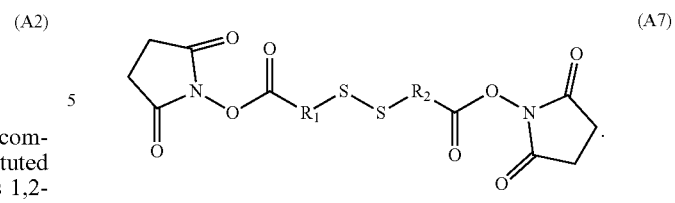
(A7)

In some embodiments, the crosslinker includes a compound of formula (A7), wherein $R_1$ and $R_2$ are unsubstituted divalent $C_1$-$C_5$ hydrocarbyls, and the crosslinker has the following structure:

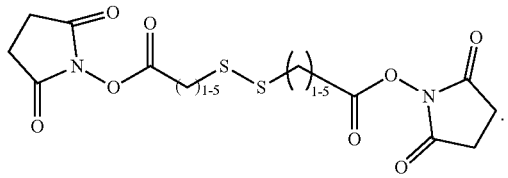
(A8)

In some embodiments, the crosslinker includes a compound of formula (A7), wherein $R_1$ and $R_2$ are unsubstituted divalent $C_2$ hydrocarbyls, and the crosslinker includes bis(2,5-dioxopyrrolidin-1-yl)3,3'-disulfanediyldipropanoate:

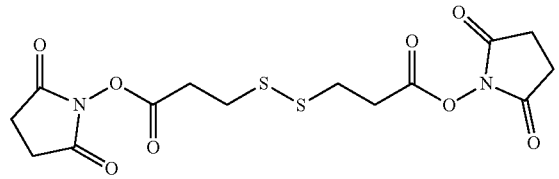

In some embodiments, the crosslinker includes the UV light sensitive moiety, and the UV light sensitive moiety is a photoreversibly dimerizable moiety. Generally, the photoreversibly dimerizable moiety is a moiety that can be activated, i.e., dimerized, when exposed to a first wavelength of light, and deactivated, i.e., cleaved, when exposed to a second wavelength of light capable of cleaving the dimer. In other words, the photoreversibly dimerizable moiety is capable of forming a dimer when exposed to a first wavelength of light, and the dimer can be cleaved when exposed to a second wavelength of light. The "first wavelength of light" and the "second wavelength of light" may independently include [1] a single wavelength of light, [2] or two or more wavelengths of light within a range of wavelengths. As used herein, the term "dimer" includes two photoreversibly dimerizable moieties that have been bonded to each other due to the application of light.

In some embodiments, the crosslinker including a photoreversibly dimerizable moiety includes coumarin. In some embodiments, the crosslinker including a photoreversibly dimerizable moiety includes a coumarin derivative. In some embodiments, the crosslinker including a photoreversibly dimerizable moiety includes 7-hydroxycoumarin.

In some embodiments, the crosslinker including a photoreversibly dimerizable moiety includes a methyl-substituted coumarin. It is believed that the use of methyl-substituted coumarin can enhance the photocleavage reaction as compared to non-methyl-substituted coumarin. There is evidence in the chemical literature indicating that the presence of a methyl substituent greatly enhances the reversibility of the coumarins (see, e.g., Chen, Y., et al. J. APPL. POLYM. SCI. 1997, 64, 1759; Chen, Y., et al. J. POLYM. SCI., PARTA: POLYM. CHEM. 1997, 35, 613; and Chen, Y., et al. J. APPL. POLYM. SCI. 1997, 64, 1749).

In some embodiments, the crosslinker including a photoreversibly dimerizable moiety includes a compound having the following structure:

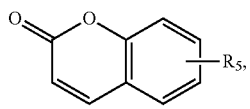
(B1)

wherein $R_5$ is a monovalent $C_1$-$C_{20}$ hydrocarbyl including a moiety capable of reacting with and covalently bonding to the polymeric carrier.

The moiety capable of reacting with and covalently bonding to the polymeric carrier may be an aldehyde, a carboxylic acid, an isocyanate, an epoxide, or an N-hydroxysuccinimide ester moiety. The crosslinker that is a compound of formula (B1) may be in "deactivated" form (i.e., the form of formula (B1)), or at least one of the following "activated" forms:

"Activated" Forms of (B1)

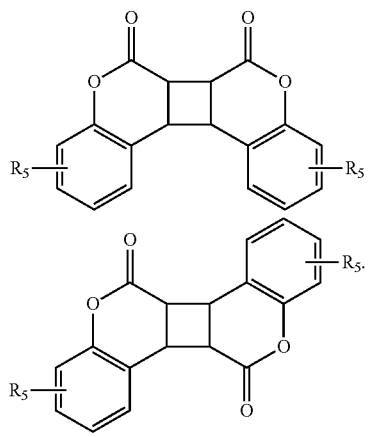

In some embodiments, the crosslinker including a photoreversibly dimerizable moiety includes a compound having the following structure:

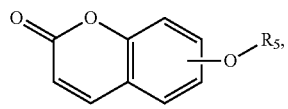
(B2)

wherein $R_5$ is a monovalent $C_1$-$C_{20}$ hydrocarbyl including a moiety capable of reacting with and covalently bonding to the polymeric carrier. The moiety capable of reacting with and covalently bonding to the polymeric carrier may be a carboxylic acid, an aldehyde, an isocyanate, an epoxide, or an N-hydroxysuccinimide ester moiety. The crosslinker that is a compound of formula (B2) may be in "deactivated" form (i.e., the form of formula (B2)), or at least one of the following "activated" forms:

"Activated" Forms of (B2)

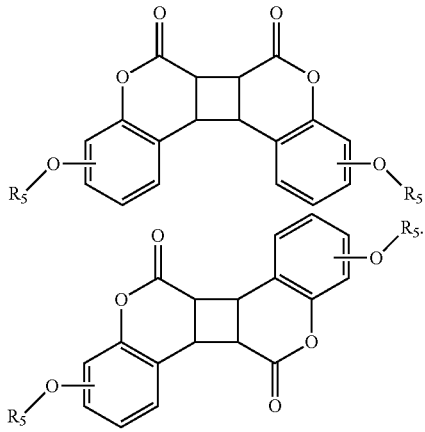

Although the "activated" forms of (B1) and (B2) have symmetrical structures, the "activated" forms of the crosslinkers including a photoreversibly dimerizable moiety may have asymmetrical structures. In other words, a first portion of the crosslinker that includes a photoreversibly dimerizable moiety may be dimerized with a second portion of the crosslinker that includes a photoreversibly dimerizable moiety, and the first portion and the second portion may have different structures. For example, a crosslinker of formula (B1) and a crosslinker of formula (B2) could be dimerized to form the one or both of the following crosslinkers:

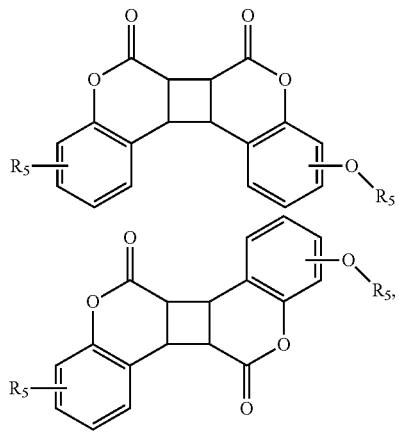

wherein each $R_5$ is independently selected from a monovalent $C_1$-$C_{20}$ hydrocarbyl including a moiety capable of reacting with and covalently bonding to the polymeric carrier.

In some embodiments, the crosslinker includes the UV light sensitive moiety, and the crosslinker is a photocleavable moiety. A photocleavable moiety is a group that may be cleaved upon exposure to a select or certain wavelength of light. The photocleavable moiety may be an o-nitrobenzene based photolabile group. The o-nitrobenzene based photolabile group may permit a crosslinker to be cleaved, because the o-nitrobenzene based photolabile group may react according to the following mechanism:

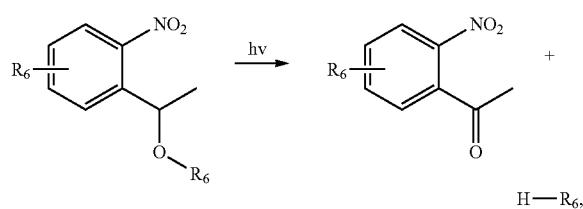

wherein each $R_6$ is independently selected from a monovalent $C_1$-$C_{20}$ hydrocarbyl including a moiety capable of reacting with and covalently bonding to the polymeric carrier. Not wishing to be bound by any particular theory, it is believed that the structure of at least one of the $R_6$ substituents may determine, at least in part, which wavelength of light is capable of cleaving the crosslinker.

In some embodiments, the crosslinker includes an o-nitrobenzene based photolabile group and a coumarin moiety. For example, the crosslinker may have the following structure, which may be photocleaved:

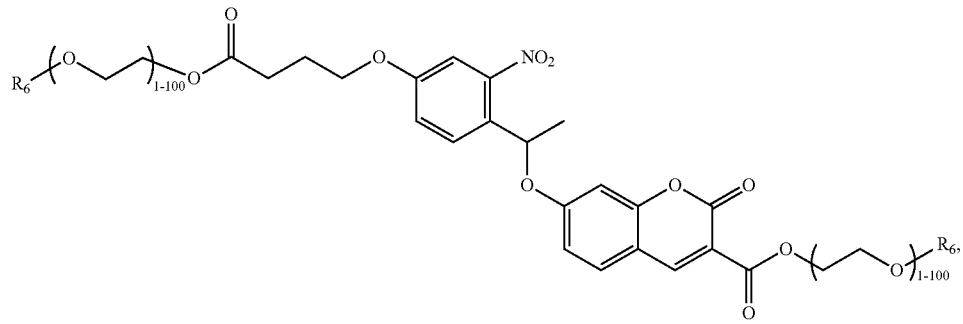

wherein each $R_6$ is independently selected from an aldehyde, a carboxylic acid, an isocyanate, an epoxide, and an N-hydroxysuccinimide ester moiety.

Degree of Crosslinking

When the polymeric carriers herein are crosslinked, a degree of crosslinking may be selected to impart the crosslinked polymeric carriers with one or more characteristics, such as altering the digestion time. The phrase "degree of crosslinking," as used herein, generally refers to the ratio of [1] the amount of crosslinker to [2] the amount of uncrosslinked polymeric carrier that is contacted with the amount of crosslinker to form the crosslinked polymeric carrier.

In some embodiments, the ratio of the crosslinker (mmol) to the polymeric carrier (g) is less than about 2.0 mmol:10 g. In some embodiments, the ratio of the crosslinker (mmol) to the polymeric carrier (g) is about 0.1 mmol:10 g to about 1.9 mmol:10 g. In some embodiments, the ratio of the crosslinker (mmol) to the polymeric carrier (g) is about 0.5 mmol:10 g to about 1.0 mmol:10 g.

Digesting Agents

The digesting agents herein generally may include one or more agents capable of [1] digesting the polymeric carrier enzymatically and/or [2] exploiting the sensitivity of one or more crosslinkers.

In some embodiments, the one or more digesting agents includes a reducing agent. In some embodiments, the one or more digesting agents includes an enzyme. In some embodiments, the one or more digesting agents includes a reducing agent and an enzyme. The reducing agent may include dithiothreitol (DTT), cysteine, glutathione, or a combination thereof. The enzyme may include collagenase, dispase-like protease, trypsin, urease, papain, bromelain, pancreatin, gelatinase (MMP2 and MMP9), or a combination thereof.

The one or more digesting agents may be in the form of a solution. For example, the one or more digestive agents may include a solution of a reducing agent, such as a solution of dithiothreitol (DTT). The digesting agent solutions may have a concentration of about 5 mM to about 25 mM. The digesting agent solutions also may include one or more additives and/or enzymes. For example, the reducing agent solution may include sodium citrate, trypsin, or a combination thereof. In some embodiments, the digesting agent is a solution of DTT having a concentration of about 5 mM to about 25 mM, and the solution includes sodium citrate, trypsin, or a combination thereof.

Cells

The cells herein may include any cells that may be adhered to the polymeric carriers, including cells that are useful in various cell therapy applications. In some embodiments, the plurality of cells includes human Mesenchymal stem cells (hMSCs). In some embodiments, the plurality of cells includes endothelial cells, pluripotent stem cells, fibroblasts, hepatocytes, myocytes, osteocytes, Schwann cells, or a combination thereof.

In some embodiments, the cells herein have a cell viability of at least 80%, at least 85% at least 90%, or at least 95% upon disassociating from the polymeric carriers, or at 1 day, 2 days, 5 days, 10 days, 20 days, or 25 days after disassociating from the polymeric carriers.

The phrases "$C_1$-$C_{20}$ hydrocarbyl," "$C_1$-$C_5$ hydrocarbyl," "$C_2$ hydrocarbyl," and the like, as used herein, generally refer to aliphatic, aryl, or arylalkyl groups containing 1 to 20, 1 to 5, or 2 carbon atoms, respectively. Examples of aliphatic groups, in each instance, include, but are not limited to, an alkyl group, a cycloalkyl group, an alkenyl group, a cycloalkenyl group, an alkynyl group, an alkadienyl group, a cyclic group, and the like, and includes all substituted, unsubstituted, branched, and linear analogs or derivatives thereof, in each instance having 1 to about 20 carbon atoms, 1 to 5 carbon atoms, 2 carbon atoms, etc. Examples of alkyl groups include, but are not limited to, methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl and dodecyl. Cycloalkyl moieties may be monocyclic or multicyclic, and examples include cyclopropyl, cyclobutyl, cyclopentyl, cyclohexyl, and adamantyl. Additional examples of alkyl moieties have linear, branched and/or cyclic portions (e.g., 1-ethyl-4-methyl-cyclohexyl). Representative alkenyl moieties include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl and 3-decenyl. Representative alkynyl moieties include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl and 9-decynyl. Examples of aryl or arylalkyl moieties include, but are not limited to, anthracenyl, azulenyl, biphenyl, fluorenyl, indan, indenyl, naphthyl, phenanthrenyl, phenyl, 1,2,3,4-tetrahydro-naphthalene, tolyl, xylyl, mesityl, benzyl, and the like, including any heteroatom substituted derivative thereof.

Unless otherwise indicated, the term "substituted," when used to describe a chemical structure or moiety, refers to a derivative of that structure or moiety wherein one or more of its hydrogen atoms is substituted with a chemical moiety or functional group such as alcohol, alkoxy, alkanoyloxy, alkoxycarbonyl, alkenyl, alkyl (e.g., methyl, ethyl, propyl, t-butyl), alkynyl, alkylcarbonyloxy (—OC(O)alkyl), amide (—C(O)NH-alkyl- or -alkylNHC(O)alkyl), tertiary amine (such as alkylamino, arylamino, arylalkylamino), aryl, aryloxy, azo, carbamoyl (—NHC(O)O-alkyl- or —OC(O)NH-alkyl), carbamyl (e.g., CONH$_2$, as well as CONH-alkyl, CONH-aryl, and CONH-arylalkyl), carboxyl, carboxylic acid, cyano, ester, ether (e.g., methoxy, ethoxy), halo, haloalkyl (e.g., —CCl$_3$, —CF$_3$, —C(CF$_3$)$_3$), heteroalkyl, isocyanate, isothiocyanate, nitrile, nitro, phosphodiester, sulfide, sulfonamido (e.g., SO$_2$NH$_2$), sulfone, sulfonyl (including alkylsulfonyl, arylsulfonyl and arylalkylsulfonyl), sulfoxide, thiol (e.g., sulfhydryl, thioether) or urea (—NHCONH-alkyl-).

EXAMPLES

The present invention is further illustrated by the following examples, which are not to be construed in any way as imposing limitations upon the scope thereof. On the contrary, it is to be clearly understood that resort may be had to various other aspects, embodiments, modifications, and equivalents thereof which, after reading the description herein, may suggest themselves to one of ordinary skill in the art without departing from the spirit of the present invention or the scope of the appended claims. Thus, other aspects of this invention will be apparent to those skilled in the art from consideration of the specification and practice of the invention disclosed herein.

Example 1

Synthesis of 1,2-bis-(2-isocyanatoethyl)disulfide (DIDS)

The crosslinker 1,2-bis-(2-isocyanatoethyl)disulfide (DIDS) was synthesized using diphosgene chemistry. 2,2'-disulfanediyldiethanamine, as shown in the following schematic, was contacted with diphosgene in the presence of 1,8-bis-(dimethylamino)-naphthalene to convert the terminal amine groups to isocyanate groups.

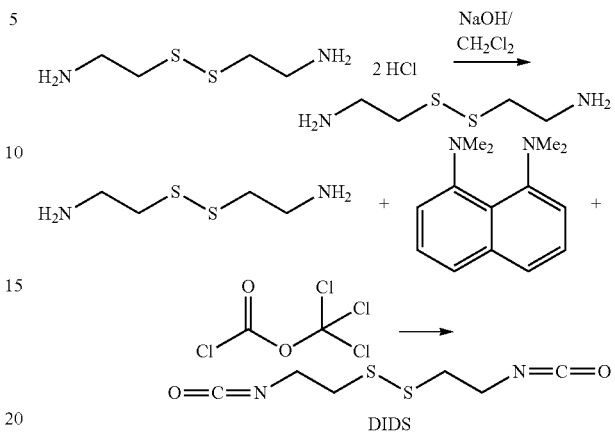

The DIDS product was then characterized by nuclear magnetic resonance spectroscopy and Fourier transform infrared spectroscopy, which confirmed the successful synthesis of the product.

Example 2

Synthesis of Redox Sensitive Beads

An embodiment of redox sensitive beads was prepared by using the redox sensitive DIDS crosslinker of Example 1.

The redox sensitive beads ("RS beads") of this example were prepared with a gelatin material, such as the gelatin material used to make Cultispher-G beads, but the typical hexamethylene diisocyanate crosslinker of Cultispher-G beads was replaced with the DIDS crosslinker of Example 1.

For comparison purposes, a sample of [1] "regular" Cultispher-G beads using the typical hexamethylene diisocyanate crosslinker ("Reg beads"), and [2] non-crosslinked Cultispher-G beads were tested.

The morphologies of the non-crosslinked beads, Reg beads, and RS beads were observed and compared using fluorescent microscopy. All of the samples were suspended in a fluorescein isothiocyanate solution (0.1 mg/mL), and incubated at 4° C. overnight before imaging.

Fluorescent images of the Reg beads, the RS beads, and the non-crosslinked beads were collected at various magnification. The fluorescent images revealed that the beads of each type had a similar size (by bright-field microscope) and porous structure (by fluorescent imaging for cross-section). These results were further confirmed by energy-dispersive X-ray assisted scanning electron microscopy (SEM-EDX). Data from SEM-EDX is depicted at Table 1.

TABLE 1

| SEM-EDX Data | | |
|---|---|---|
| Element | Reg Bead (% of element) | RS Bead (% of element) |
| C | 75.26 | 70.98 |
| N | 11.84 | 10.46 |
| O | 11.61 | 16.50 |
| S | 1.29 | 2.06 |

The difference in the sulfur content of the Reg beads and the RS beads depicted at Table 1 indicated the presence of the disulfide bonds of the DIDS crosslinker.

Figure 1B:
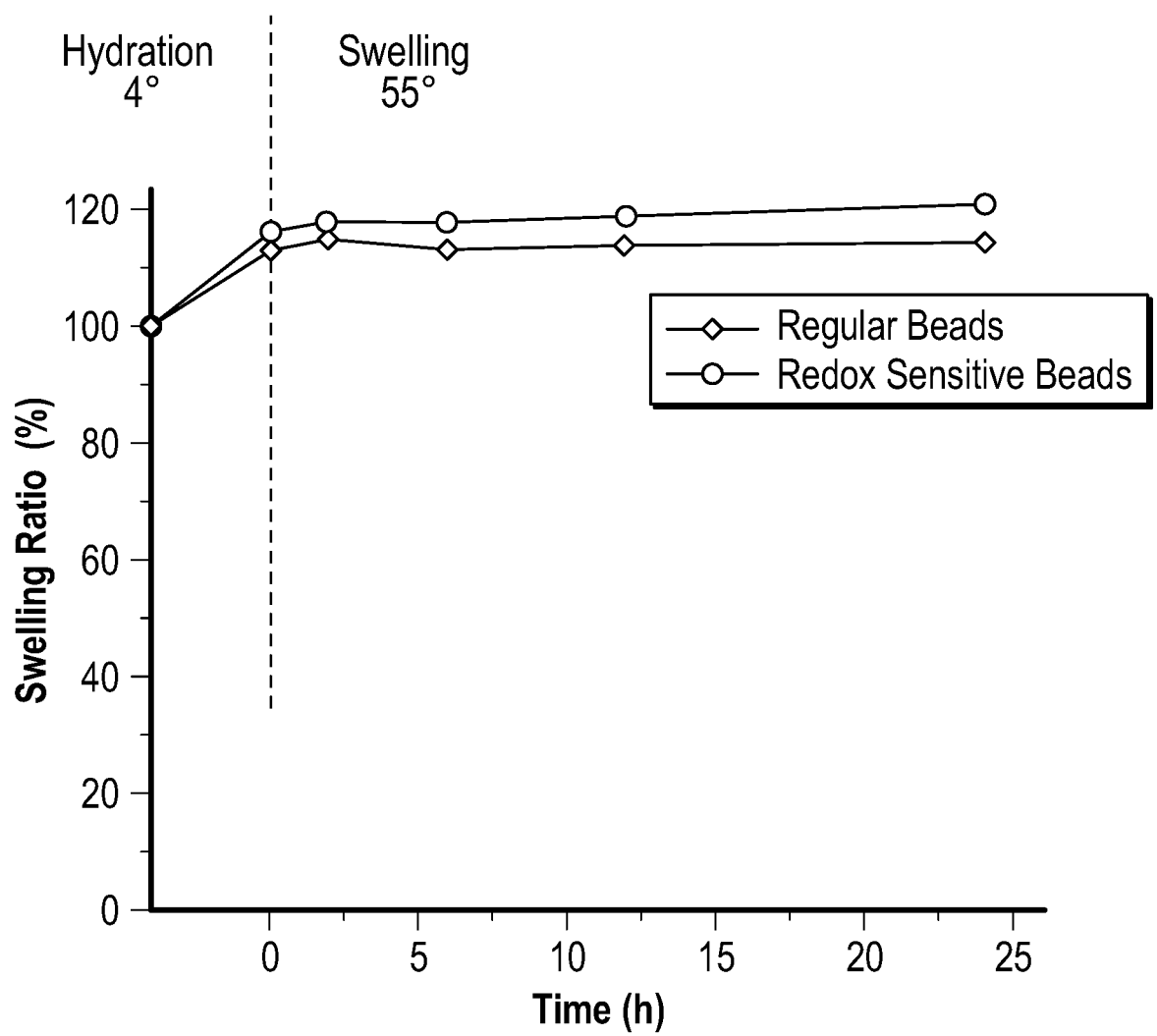
FIG. 1B depicts the results of a swelling ratio study conducted on two types of Cultispher-G beads, including an embodiment of a redox sensitive Cultispher-G bead.

The physical properties of the Reg beads and RS beads were further characterized by gelatin extraction and swelling ratio studies in Dulbecco's phosphate buffered saline (DPBS), without $Ca^{2+}$ and $Mg^{2+}$. As indicated by FIG. 1A and FIG. 1B, no significant differences in extraction percentage (FIG. 1A) or swelling ratio (FIG. 1B) were observed, which demonstrated that the RS beads of Example 1 and the Reg beads had similar crosslinking degrees and hydrophilicity.

Example 3

In Vitro Digestion Study

Figure 2:
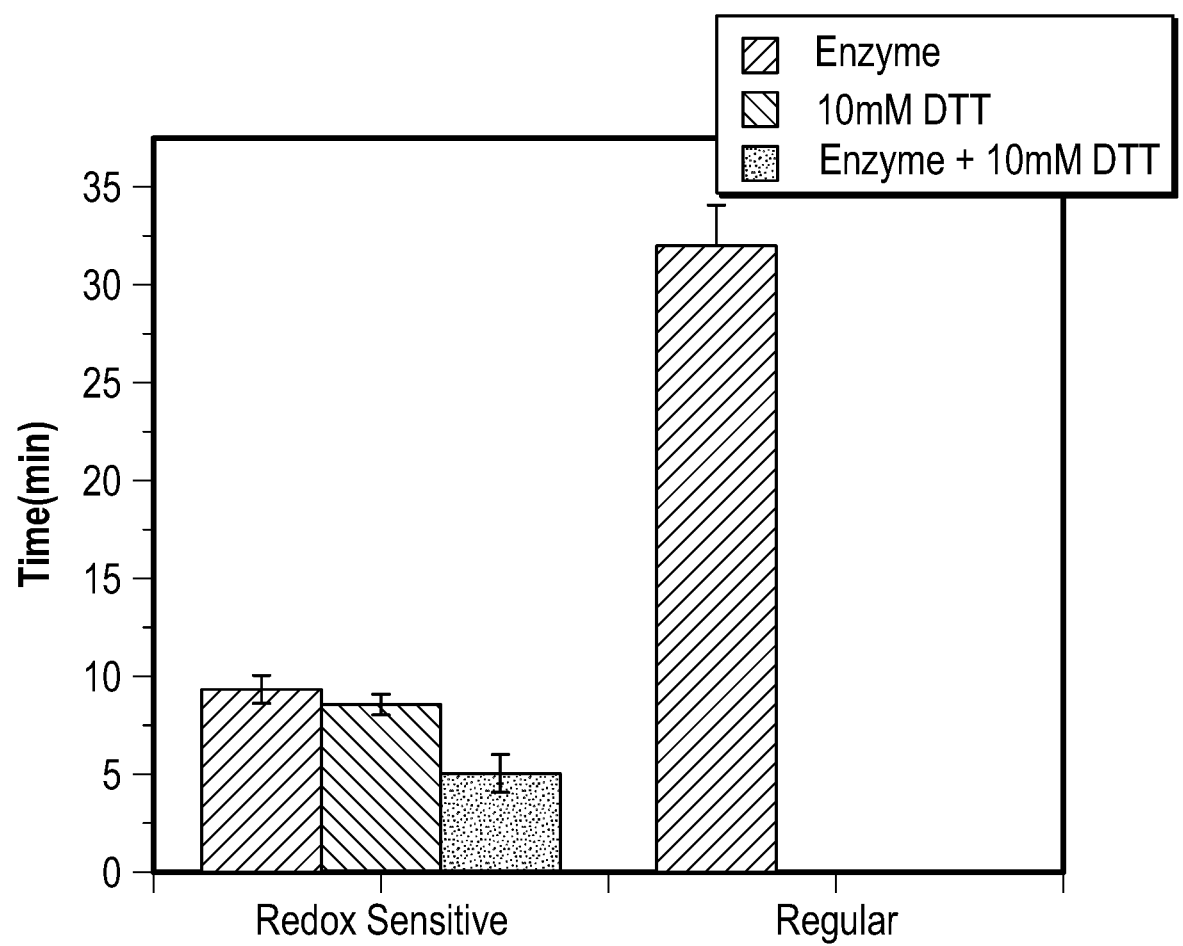
FIG. 2 depicts the cell-free digestion time of two types of Cultispher-G beads, including an embodiment of a redox sensitive Cultispher-G bead.

Cell-free digestion time was measured for the Reg beads and RS beads of Example 1, and the results are depicted at FIG. 2. Full digestion was reached for the Reg beads after about 30 minutes in an enzyme solution. The Reg beads, as expected, were not digested by the dithiothreitol (DTT) solution (10 mM DTT), or the DTT/enzyme digestion solution. However, the DTT solution digestion time was only about 8 minutes for the RS beads, and the RS beads also digested significantly faster (about 9 minutes) in the enzyme solution compared to the Reg beads (about 30 minutes).

Example 4

In Vitro Cytotoxicity Study

The cytotoxicity of the digestion solution and the digestion products of the RS beads of Example 3 were studied by MTT assay (MTT-3-(4,5-dimethylthiazol-2-yl)-2,5-diphenyltetrazolium bromide).

Figure 3A:
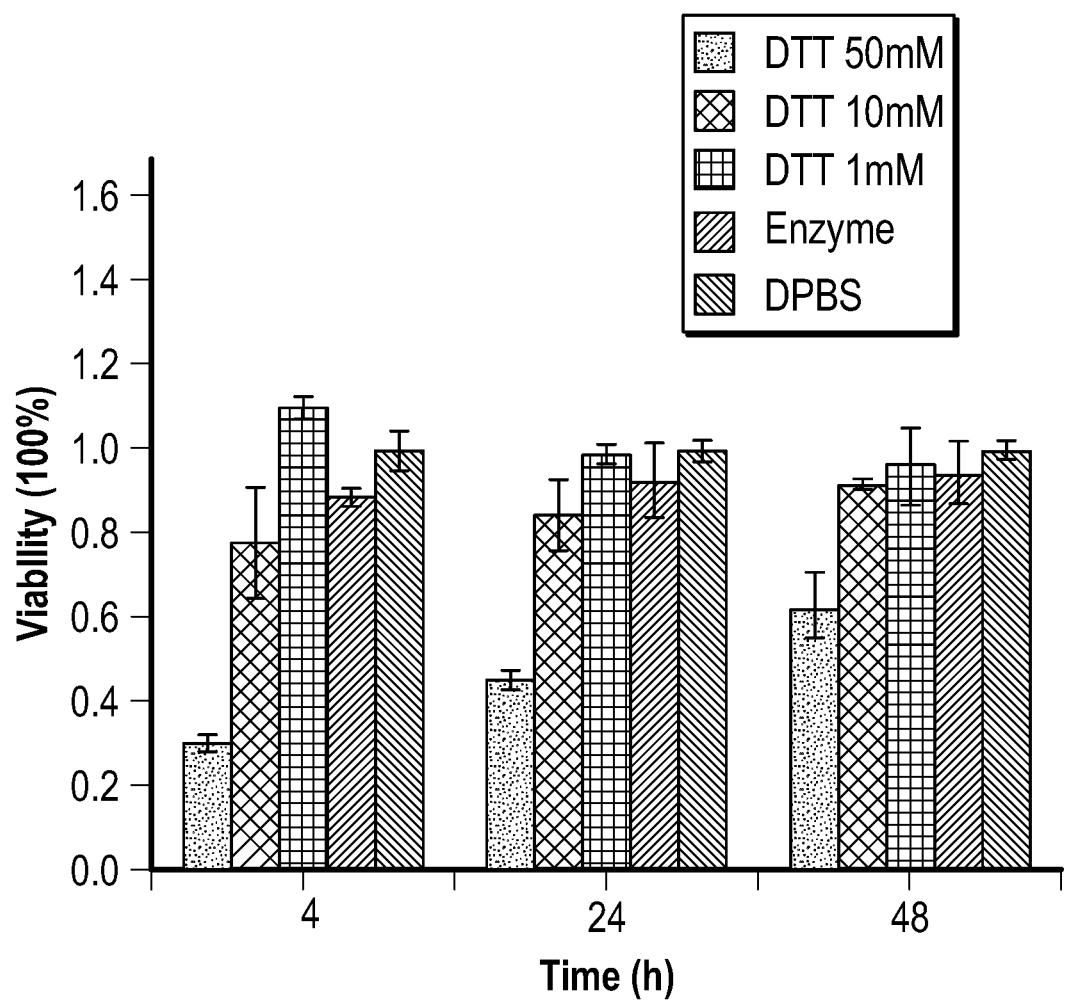
FIG. 3A depicts the cytotoxicity of digestion solutions obtained from the digestion of an embodiment of a redox sensitive bead.

In this example, 3T3 fibroblasts were used as model cells. The results, as depicted at FIG. 3A, indicated that only the 50 mM DTT solution showed significant cytotoxicity. DTT at the working concentration (10 mM), the low concentration (1 mM), and an enzyme solution showed no significant cytotoxicity compared to DPBS.

Figure 3B:
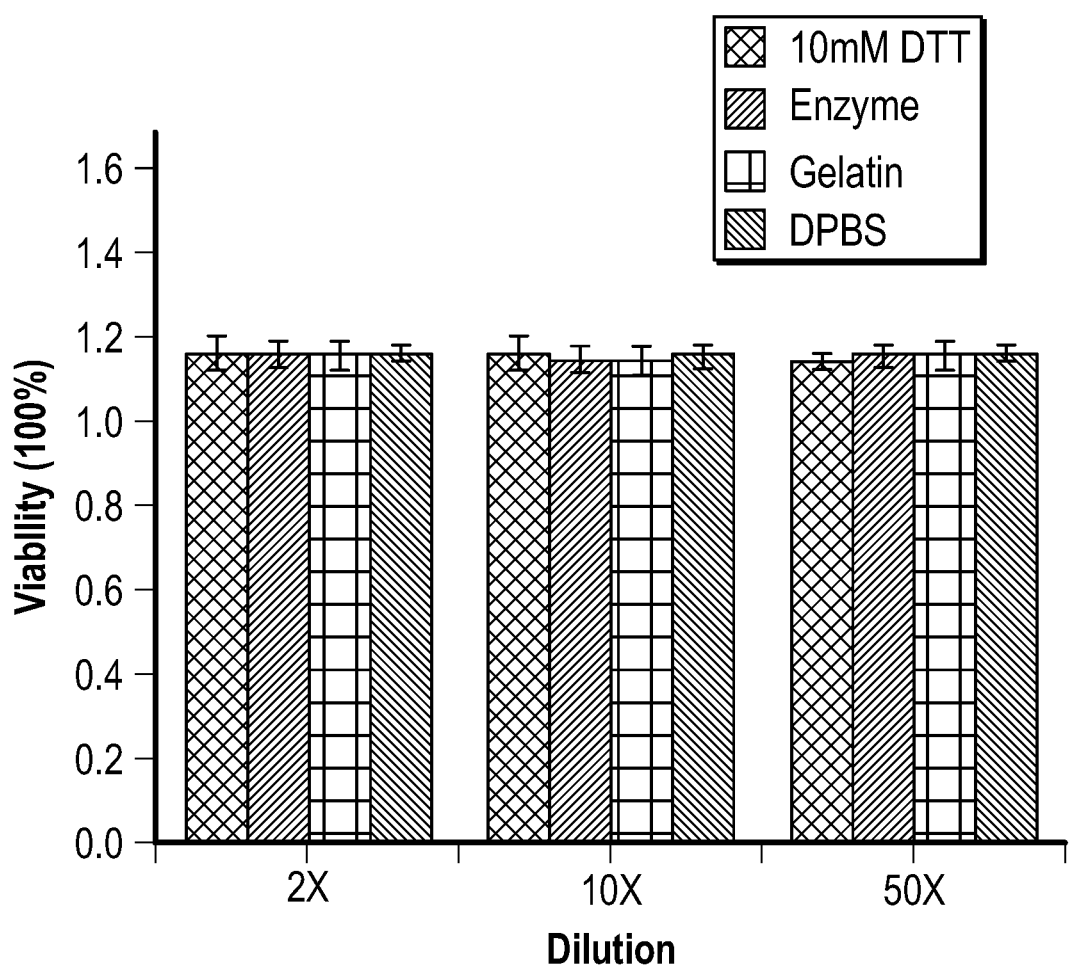
FIG. 3B depicts the cytotoxicity of different concentrations of digestion solutions obtained from the digestion of an embodiment of a redox sensitive bead.
Figure 3C:
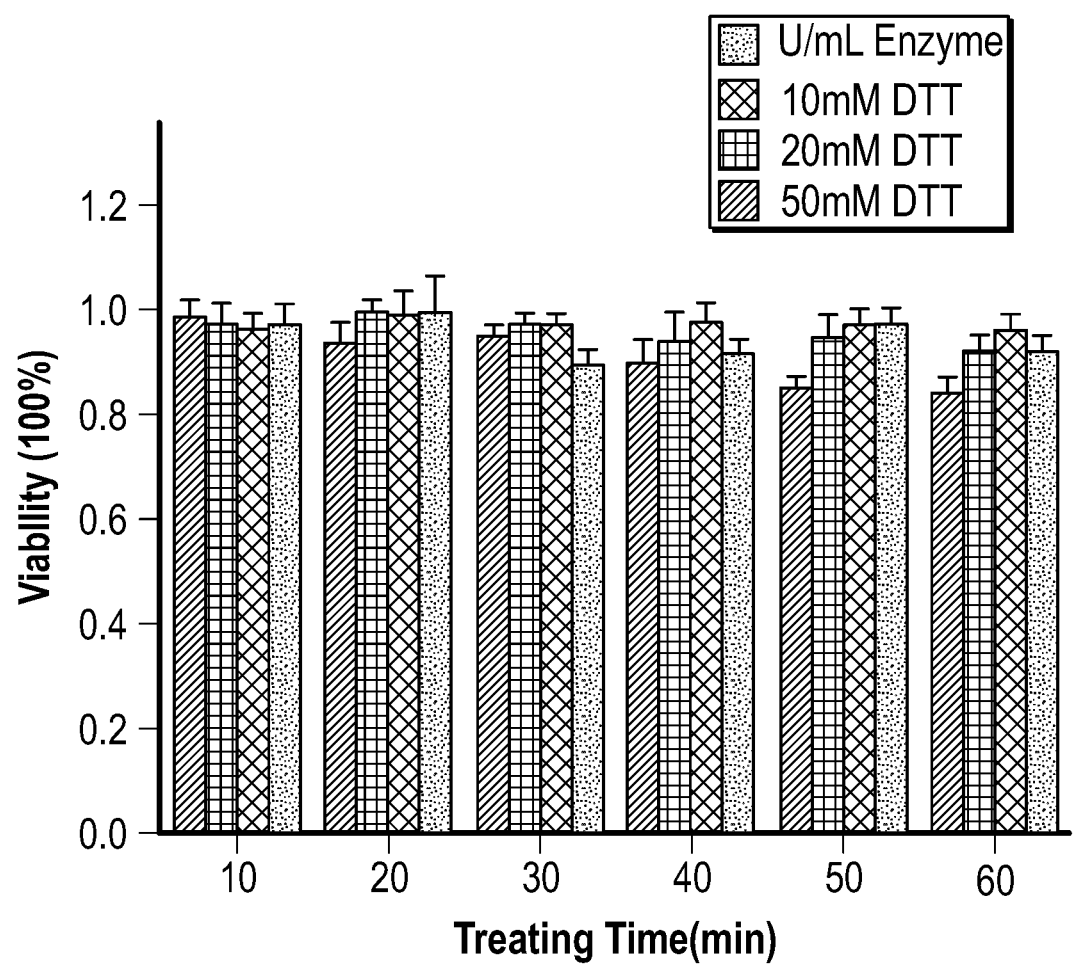
FIG. 3C depicts the tolerance of human Mesenchymal stem cells to digestion solutions obtained from the digestion of an embodiment of a redox sensitive bead.

Based on the results depicted at FIG. 3B, it was concluded that the digestion products of the RS sensitive beads of Example 3 showed no sign of cytotoxicity at either concentration after 4 hours. Also, the DTT cytotoxicity to human mesenchymal stem cells (hMSC) was studied, as depicted at FIG. 3C. The data at FIG. 3C demonstrated that with short exposure (<30 minutes), hMSC was tolerant to all digestion solutions, even with a high concentration of DTT (50 mM). With longer exposure, hMSC presented low viability—80% to 85%—at the high concentration of DTT (50 mM).

Example 5

Spinning Culture of hMSCs and Digestion Studies

Figure 4A:
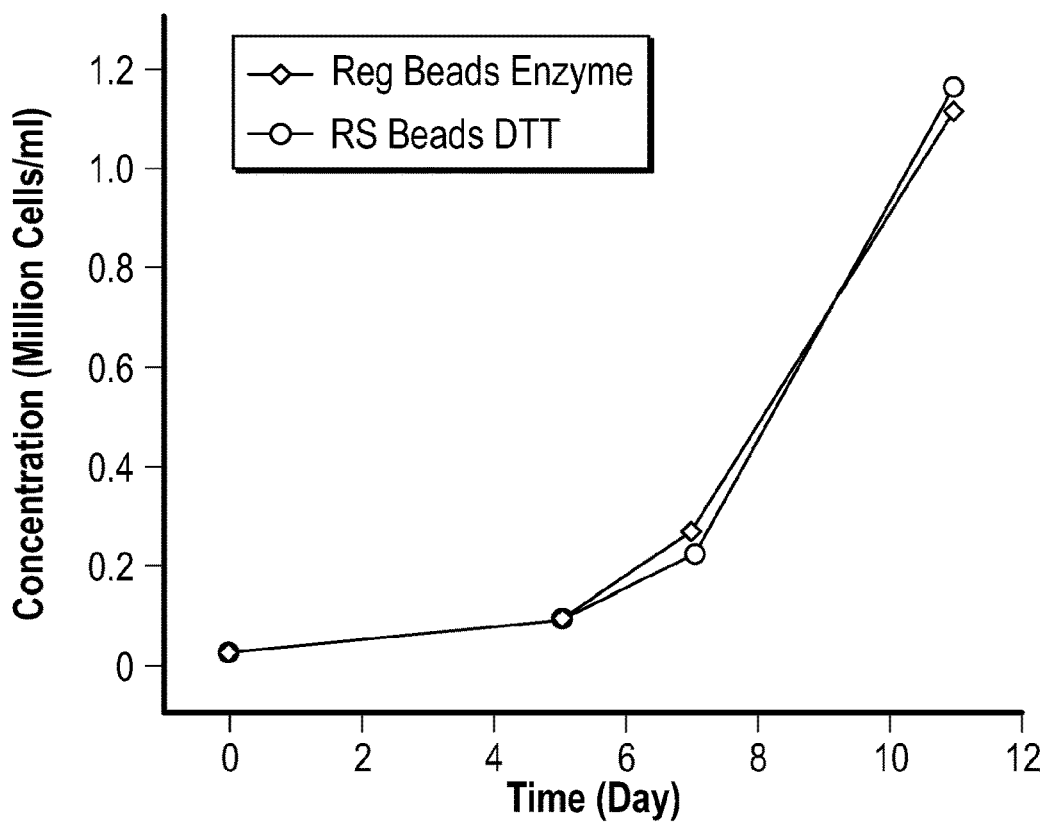
FIG. 4A depicts the concentration of cells over 12 days on two types of carriers, including an embodiment of a redox sensitive bead.

In spinner flasks, hMSCs were cultured on the Reg beads and RS beads of Example 1. The cell count results for both runs, as shown at FIG. 4A and FIG. 4C, indicated that the hMSCs had similar growth rates on the Reg beads and the RS beads. These results were believed to demonstrate the ability of the RS beads of Example 1 to serve as a cell carrier for hMSCs. The high cell number that occurred after day 6 of FIG. 4A and FIG. 4C were confirmed by (4',6-diamidino-2-phenylindole)(i.e., DAPI) staining.

Figure 4B:
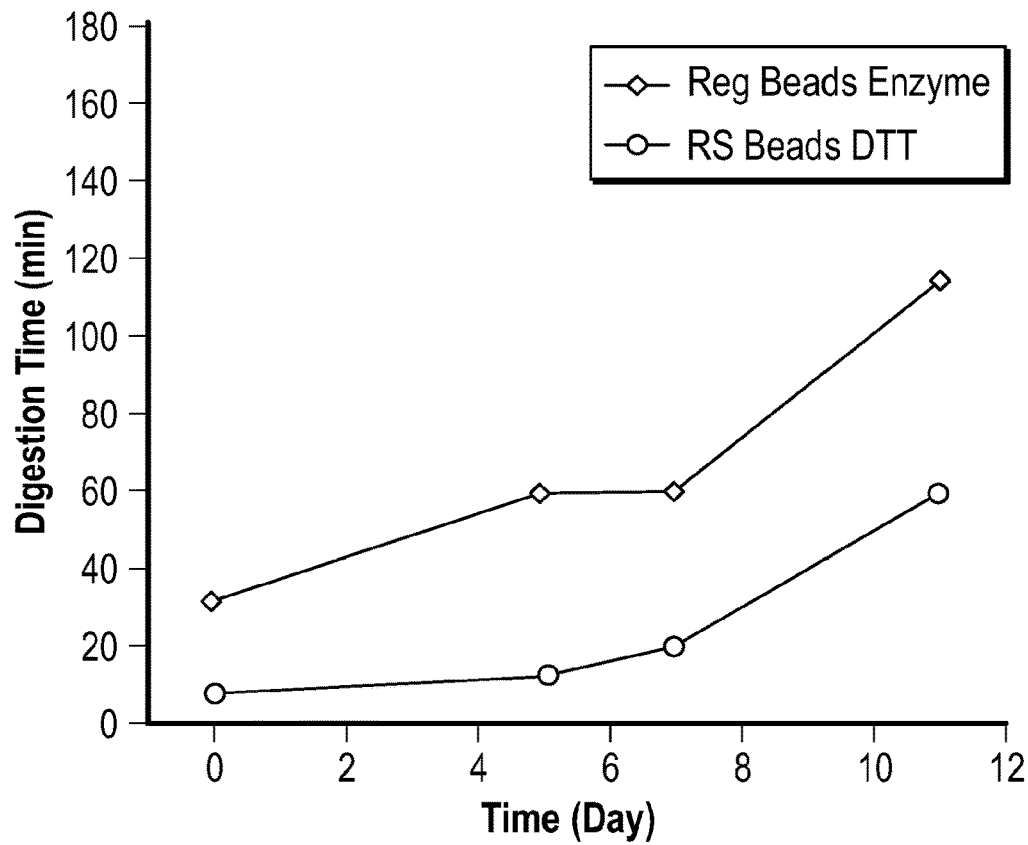
FIG. 4B depicts the digestion time over 12 days for two types of carriers, including an embodiment of a redox sensitive bead.
Figure 4C:
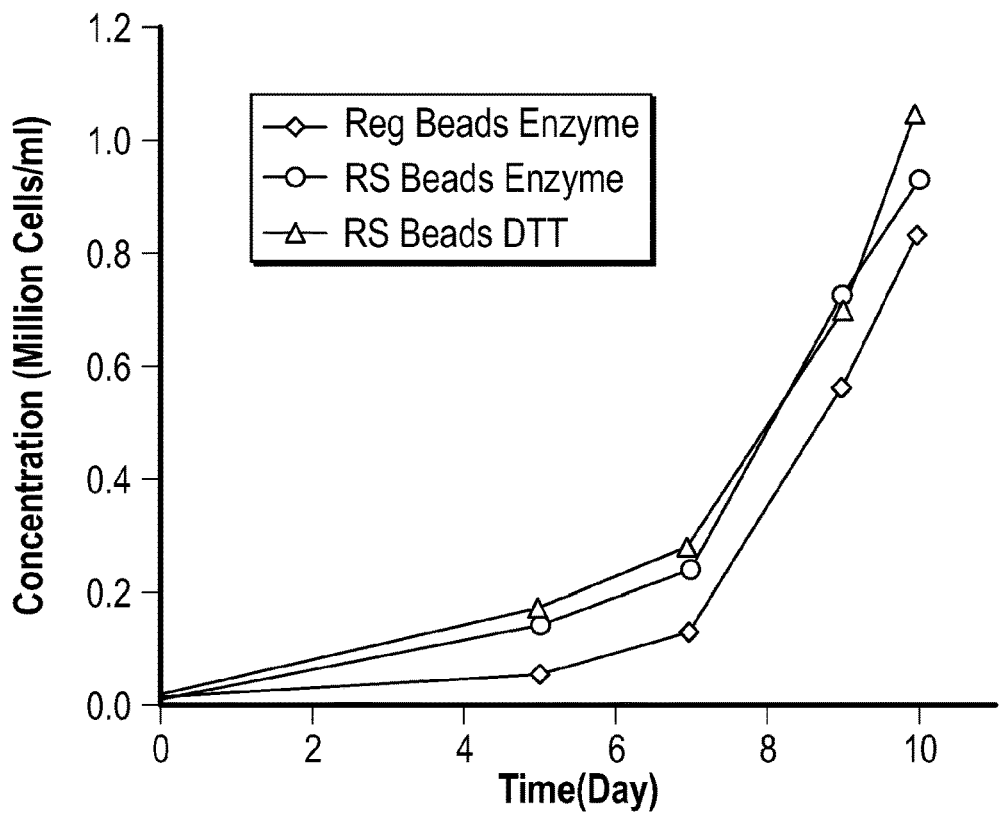
FIG. 4C depicts the concentration of cells over 10 days upon treatment of two types of carriers, including one embodiment of a redox sensitive bead, with several embodiments of digesting agents.
Figure 4D:
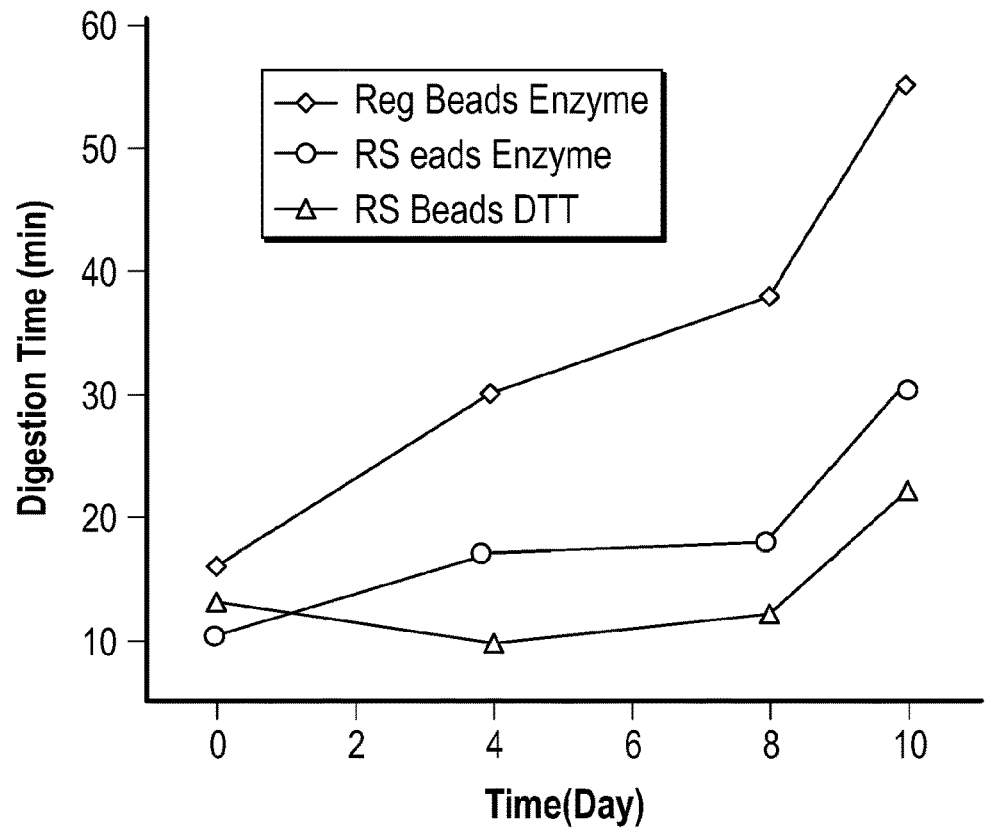
FIG. 4D depicts the digestion time over 10 days upon treatment of two types of carriers, including an embodiment of a redox sensitive bead, with several embodiments of digesting agents.

Also, the digestion times of the Reg beads and RS beads of FIG. 4A and FIG. 4C demonstrated, as shown at FIG. 4B and FIG. 4D, respectively, that the digestion time increased as the cell density increased.

At the day of harvest, bead samples of each type were collected, dyed, and sectioned for fluorescence microscopy, which revealed that the cells proliferated and penetrated into both the Reg beads and the RS beads.

Example 6

Photocrosslinked Beads

Photocrosslinked Cultispher-G beads were formed by conjugating coumarin onto non-crosslinked Cultispher-G beads. The beads were then crosslinked via coumarin photodimerization (365 nm), as verified by their insolubility in water at 37° C.

Figure 5:
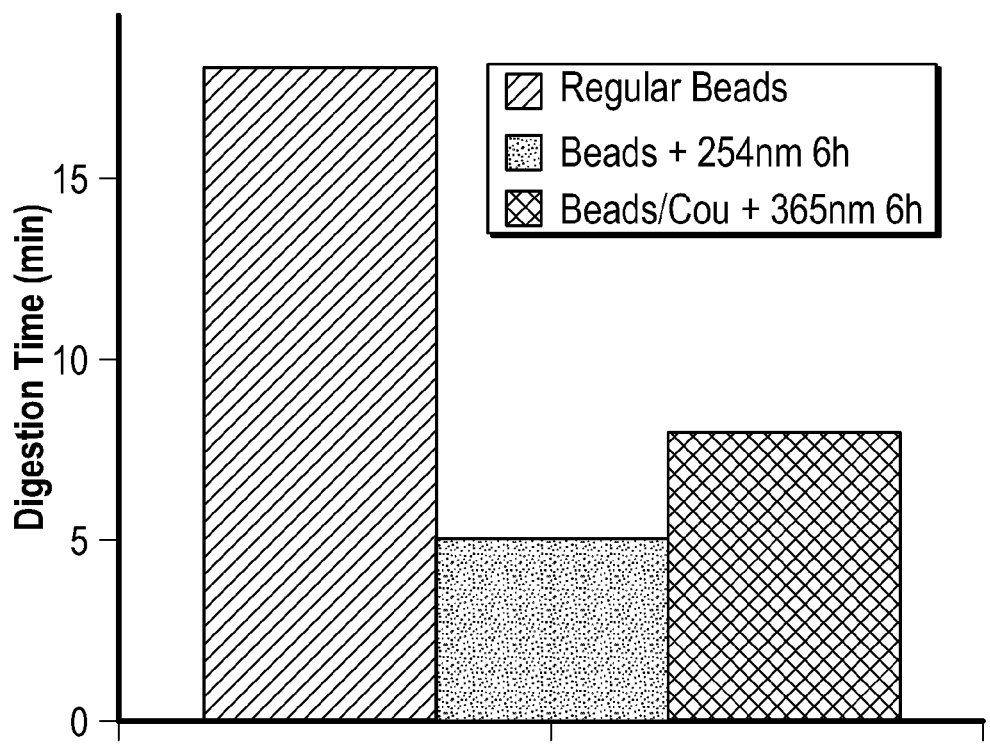
FIG. 5 depicts the enzymatic digestion time (minutes) of an embodiment of photocrosslinked Cultispher-G beads conjugated with a coumarin derivative, photocrosslinked Cultispher-G beads without a coumarin derivative, and Cultispher-G beads crosslinked with the typical hexamethylene diisocyanate.

The photocrosslinked beads were then digested enzymatically, along with a sample of the Reg beads of Example 1. The photocrosslinked beads digested enzymatically in less time than the Reg beads, as depicted at FIG. 5. Moreover, due to the UV-induced free radical crosslinking of gelatin, a sample of the Cultispher-G beads (with no coumarin) was crosslinked by using UV irradiation (254 nm) directly. These beads also digested enzymatically faster than the Reg beads, as depicted at FIG. 5.

Example 7

Effect of Degree of Crosslinking

Cultispher-G beads having a lower degree of crosslinking (LC beads) were fabricated by lowering the ratio of hexamethylene diisocyanate crosslinker to beads. This ratio was 2 mmol crosslinker to 10 g of beads for the Reg beads of Example 1. LC beads were fabricated at ratios of 1 mmol to 10 g of beads, and 0.5 mmol to 10 g of beads. A hexamethylene diisocyanate crosslinker was used in this example, because Cultispher-G beads typically are crosslinked with this crosslinker to provide a thermally stable structure for cell culture application.

The LC beads of this example had good thermal stability under 55° C. The Reg beads and LC beads of this example were then subjected to a cell-free enzymatic digestion study. The digestion was achieved in this example with an enzyme solution of collagenase and protease.

Figure 6:
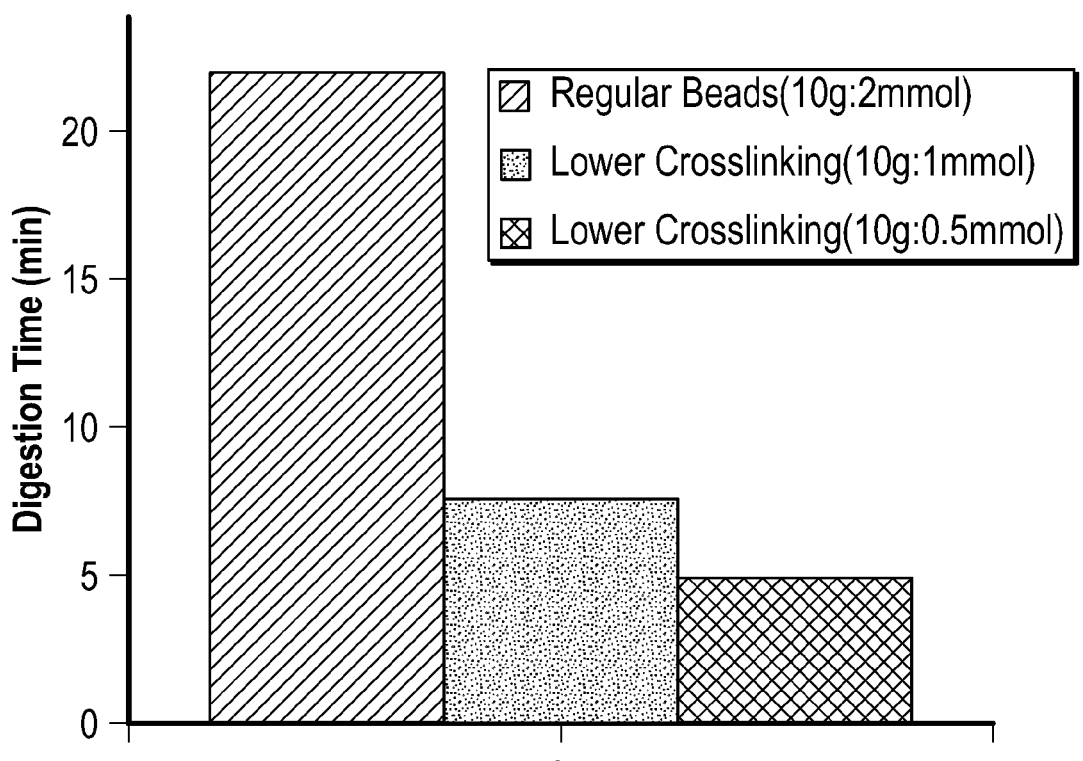
FIG. 6 depicts the digestion times of embodiments of Cultispher-G beads having different degrees of crosslinking.

As depicted at FIG. 6, the digestion time for the LC beads of this example was significantly reduced compared to the digestion time of the Reg beads. By reducing the degree of crosslinking by half, the digestion time was reduced from 22 minutes for the Reg beads (10 g beads:2 mmol crosslinker) to 7.5 minutes for the LC beads (10 g beads:1 mmol crosslinker). The digestion time was further reduced to about 5 minutes for the LC beads having a degree of crosslinking that had been reduced by 75%, i.e., (10 g beads:0.5 mmol crosslinker). These results demonstrated that reducing the degree of crosslinking reduced the enzymatic digestion time.

Figure 7A:
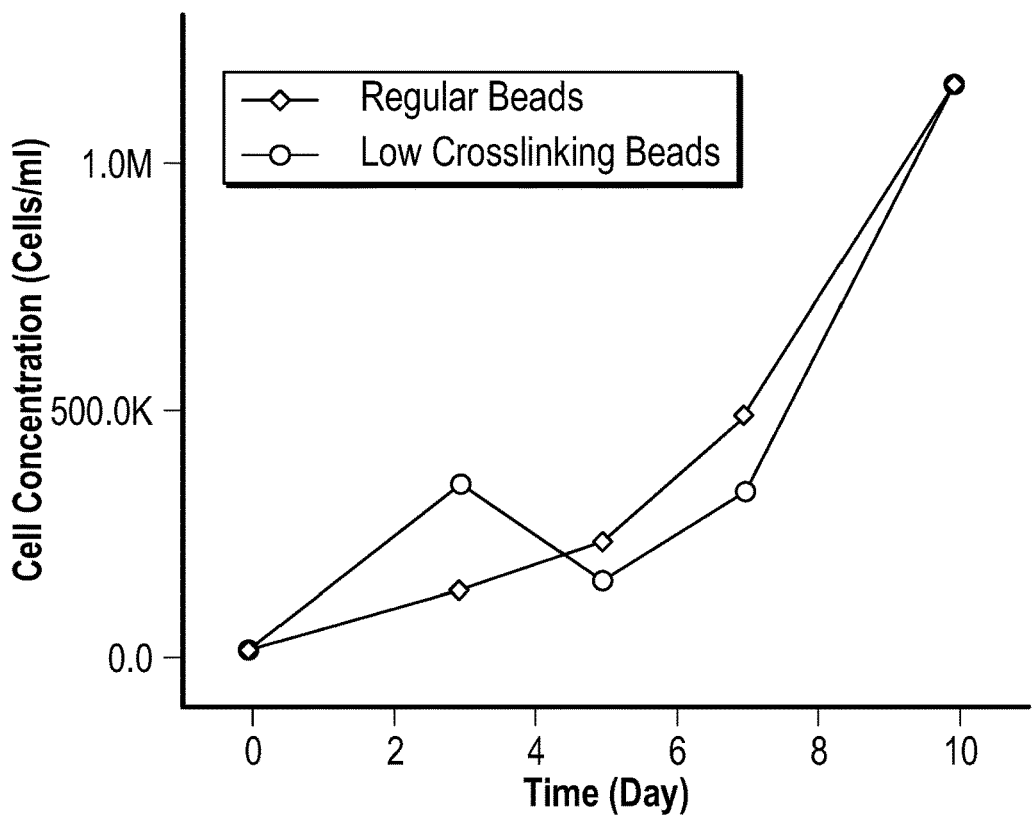
FIG. 7A depicts the cell concentration observed for embodiments of Cultsipher-G beads having different degrees of crosslinking.

The LC beads of this example were further subjected to a spinning cell culture study with hMSC. As depicted at FIG. 7A, the hMSCs had similar proliferation rates on the Reg beads and LC beads over 10 days. This was believed to demonstrate the ability of the LC beads of this example to serve as a cell carrier for hMSCs. The crosslinker:bead ratio for the LC beads of FIG. 7A was 1 mmol crosslinker to 10 g of beads.

Figure 7B:
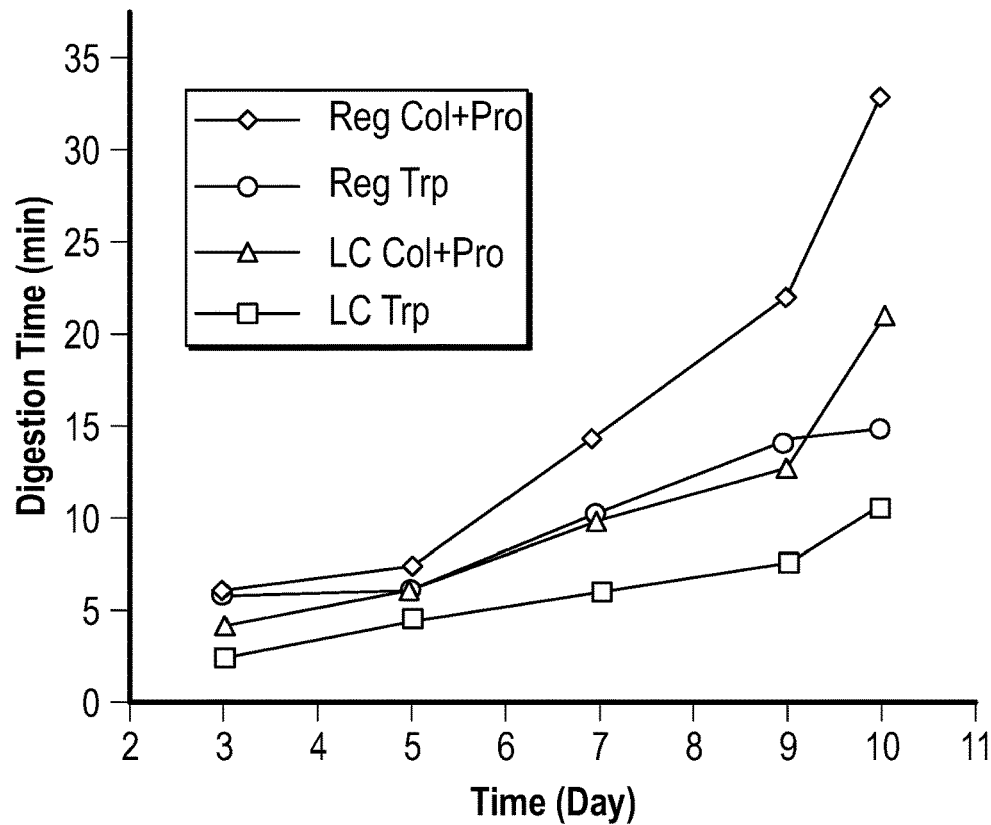
FIG. 7B depicts the digestion times for embodiments of Cultispher-G beads having different degrees of crosslinking.

The cell proliferation on the beads was also confirmed by increased digestion time, as depicted at FIG. 7B, and DAPI staining. The results of the digestion study demonstrated that the LC beads of this example digested significantly faster than the Reg beads when using the same digesting agents. The digesting agents were [1] a mixture of collagenase and protease, and [2] trypsin. The results of the spinning cell culture study of this example were believed to indicate that the LC beads conferred faster enzymatic digestion than the Reg beads, while still supporting the growth of at least substantially the same amount of cells.

Example 8

Test of Digestion Agents

Digestion agents containing DTT with other digestion agents, such as trypsin and sodium citrate buffer were tested on the RS beads of Example 1.

Figure 8A:
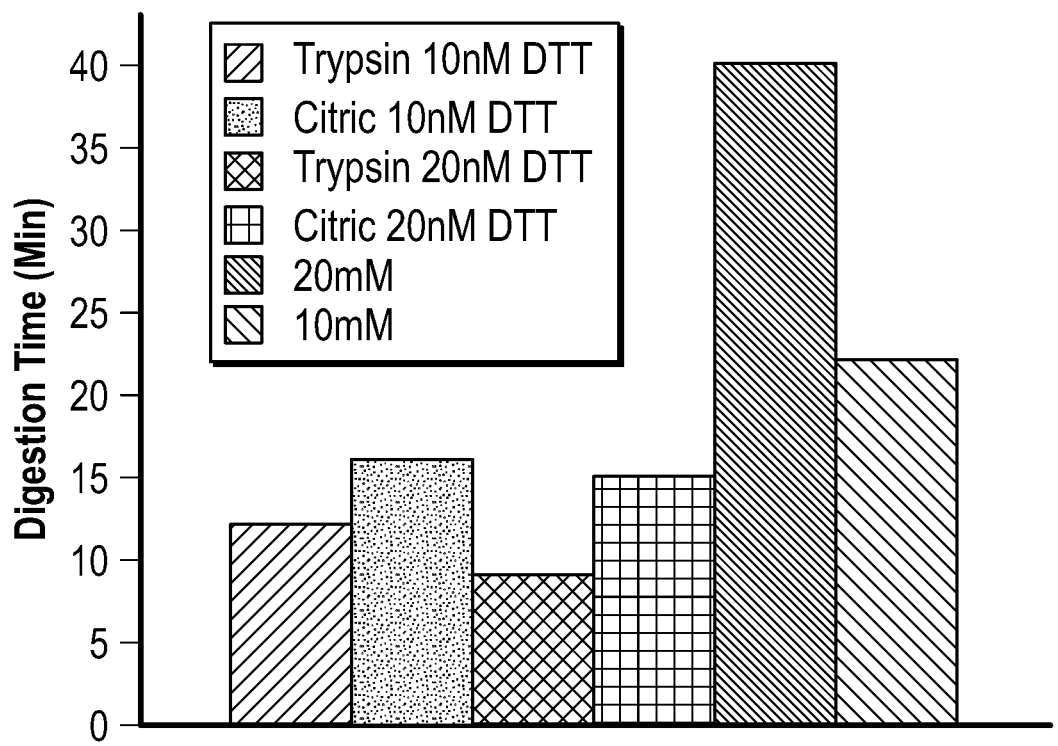
FIG. 8A depicts the digestion times observed when an embodiment of a redox sensitive bead was digested with various digestion agents.

As depicted at FIG. 8A, the results indicated that both trypsin (0.025%) and sodium citrate (0.015 M) were able to improve DTT digestion for the RS beads of Example 1. The digestion time was reduced from 22 minutes for 10 mM DTT to 16 minutes with sodium citrate and 10 mM DTT, and 12 minutes with trypsin and 10 mM DTT. The digestion time also was reduced from 40 minutes for 20 mM DTT to 15 minutes with sodium citrate and 20 mM DTT, and 9 minutes with trypsin and 20 mM DTT.

Figure 8B:
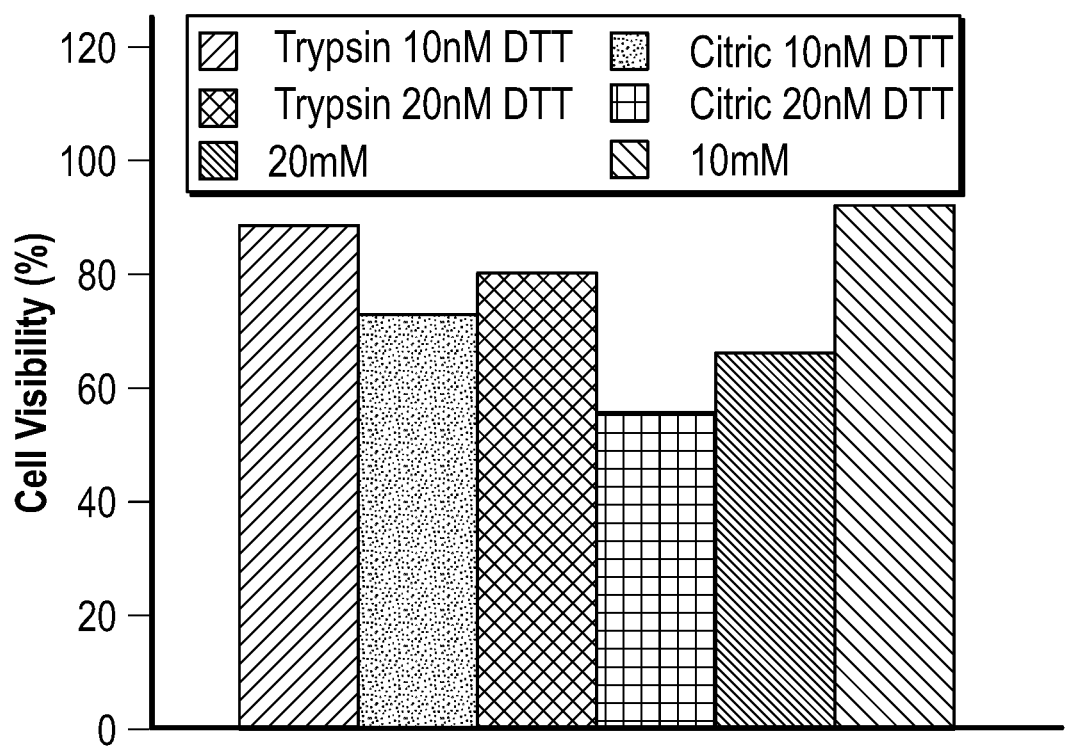
FIG. 8B depicts the cell viabilities observed after an embodiment of a redox sensitive bead was digested with different embodiments of digestion agents.

The cell viability was calculated after full digestion due to the concern of potential cytotoxicity from the digestion agents. The results depicted at FIG. 8B demonstrate that the cell viability appeared to depend heavily on the exposure time to the digestion agent solution. For example, a 40 minute exposure to 20 mM DTT significantly affected cell viability. Also, 0.015 M sodium citrate solutions displayed a certain level of cytotoxicity to the hMSCs. It was observed that with a 12 minute exposure to 0.025% trypsin and 10 mM DTT, hMSCs still had a cell viability of over 85%.

Although the digestion time was reduced to 8 minutes with the digestion agent that included a mixture of 20 mM DTT and 0.025% trypsin, as shown at FIG. 8A, the cell viability after digestion was only 80.36%. When the DTT concentration was lowered to 10 mM, the digestion time increased to 12 minutes, but the cell viability increased to 88.40%.

When an even milder digestion agent was used, such as 10 mM DTT alone or an enzyme alone, then the digestion time was significantly longer (22 minutes to 56 minutes), but the cell viability was increased to at least 95%.

Figure 9:
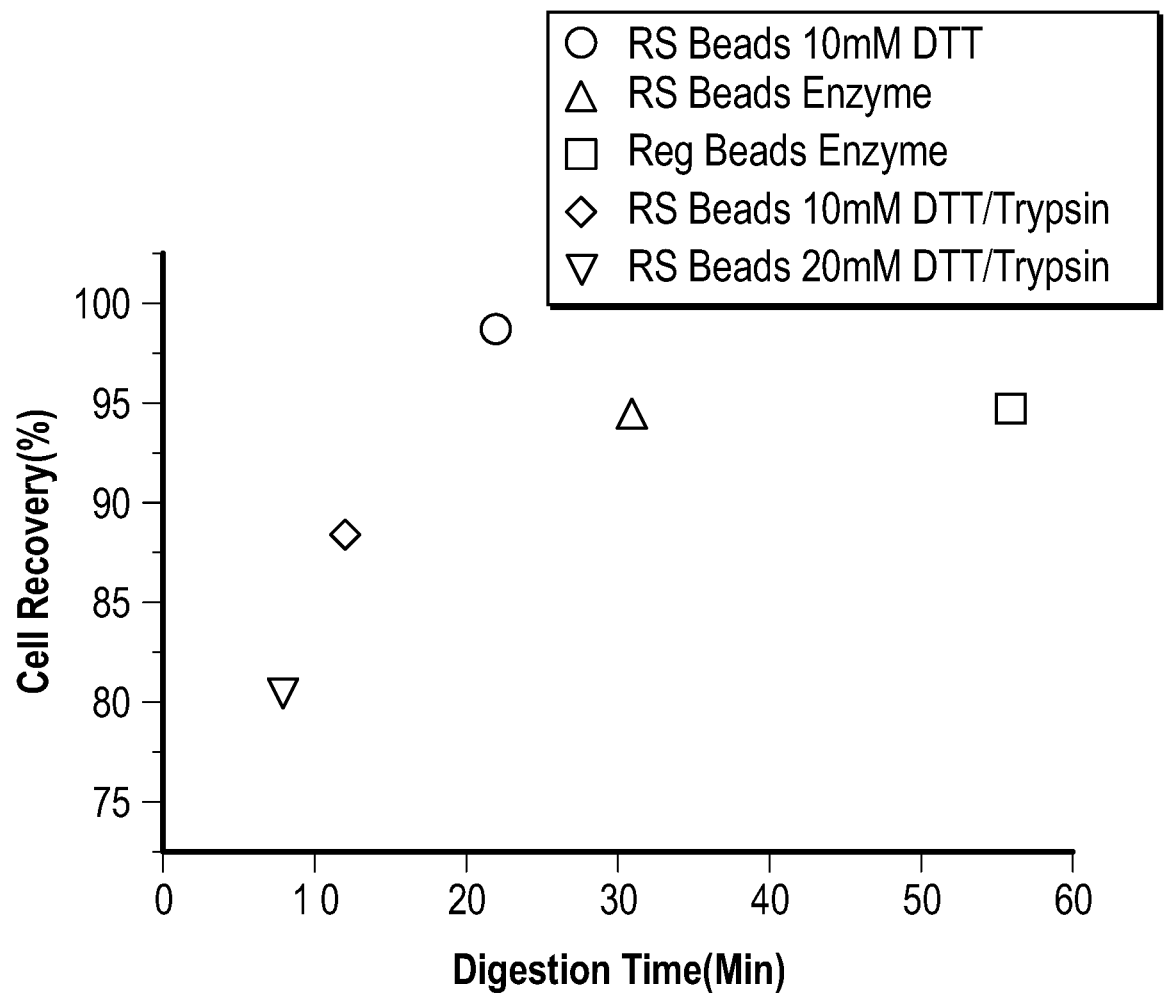
FIG. 9 depicts a plot of cell recovery versus digestion time for several embodiments of polymeric carriers.

The digestion time and cell recovery percentage of several digestion agents are depicted at FIG. 9.

The invention claimed is:

1. A method of controlling disassociation of cells from a carrier, the method comprising:
providing a polymeric carrier and a plurality of cells adhered to the polymeric carrier, wherein the polymeric carrier is a microcarrier; and
contacting the polymeric carrier with one or more digesting agents to disassociate at least a portion of the plurality of cells from the polymeric carrier;
wherein the polymeric carrier comprises gelatin, and is crosslinked with a crosslinker comprising at least one redox sensitive moiety, wherein the at least one redox sensitive moiety comprises a disulfide bond, and the crosslinker comprises a compound having the following structure—

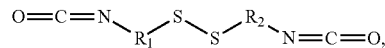

wherein $R_1$ and $R_2$ are independently selected from a divalent $C_1$-$C_{20}$ hydrocarbyl.

2. The method of claim 1, wherein $R_1$ and $R_2$ are unsubstituted divalent $C_1$-$C_5$ hydrocarbyls, and the crosslinker has the following structure:

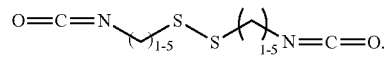

3. The method of claim 1, wherein $R_1$ and $R_2$ are unsubstituted divalent $C_2$ hydrocarbyls, and the crosslinker comprises 1,2-bis-(2-isocyanatoethyl)disulfide (DIDS):

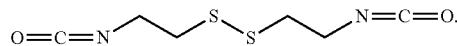

4. The method of claim 1, wherein the plurality of cells comprises human Mesenchymal stem cells (hMSCs), endothelial cells, or a combination thereof.

5. The method of claim 1, wherein the polymeric carrier further comprises dextran, hyaluronic acid, agarose, chitosan, alginate, polyvinyl alcohol, polyamino acid, calcium alginate, polyacrylate, polyethylene glycol, polyethylene imine, polyanhydride, or a combination thereof.

6. The method of claim 1, wherein the polymeric carrier further comprises dextran, hyaluronic acid, agarose, chitosan, alginate, polyvinyl alcohol, polyamino acid, or a combination thereof.

7. The method of claim 1, wherein the polymeric carrier is a polymeric carrier bead.

8. The method of claim 1, wherein the one or more digesting agents comprises a reducing agent.

9. The method of claim 8, wherein the reducing agent comprises dithiothreitol (DTT), cysteine, glutathione, or a combination thereof.

10. The method of claim 8, wherein the reducing agent comprises a solution of dithiothreitol (DTT) having a concentration of about 5 mM to about 25 mM.

11. The method of claim 10, wherein the solution of dithiothreitol further comprises sodium citrate, trypsin, or a combination thereof.

12. The method of claim 1, wherein the one or more digesting agents comprises an enzyme.

13. The method of claim 12, wherein the enzyme comprises collagenase, dispase-like protease, trypsin, urease, papain, bromelain, pancreatin, gelatinase (MMP2 and MMP9), or a combination thereof.

14. The method of claim 1, wherein the one or more digesting agents comprises a reducing agent and an enzyme.

15. The method of claim 1, wherein the ratio of the crosslinker (mmol) to the polymeric carrier (g) is about 0.1 mmol:10 g to about 1.9 mmol:10 g.

* * * * *